US008571806B2

(12) United States Patent
Desmet et al.

(10) Patent No.: US 8,571,806 B2

(45) Date of Patent: Oct. 29, 2013

(54) METHOD FOR GENERATING INFORMATION RELATED TO THE MOLECULAR STRUCTURE OF A BIOMOLECULE

(75) Inventors: Johan Desmet, Kortrijk (BE); Ignace Lasters, Antwerpen (BE); Dominique Vlieghe, Kortrijk (BE); Carlo Boutton, Zwevegem (BE); Philippe Stas, Welle (BE); Jan Spriet, Kortrijk (BE)

(73) Assignee: Lonza Biologies PLC, Slough (GB)

( * ) Notice: Subject to any disclaimer, the term of this patent is extended or adjusted under 35 U.S.C. 154(b) by 0 days.

(21) Appl. No.: 12/959,224

(22) Filed: Dec. 2, 2010

(65) Prior Publication Data

US 2011/0137617 A1 Jun. 9, 2011

Related U.S. Application Data

(62) Division of application No. 10/129,516, filed as application No. PCT/EP00/10921 on Nov. 3, 2000.

(60) Provisional application No. 60/163,408, filed on Nov. 3, 1999.

(30) Foreign Application Priority Data

Sep. 25, 2000 (WO) ...................... PCT/EP00/09460

(51) Int. Cl.
*G01N 33/48* (2006.01)
*G06G 7/48* (2006.01)

(52) U.S. Cl.
USPC .............................................. 702/19; 703/11

(58) Field of Classification Search
None
See application file for complete search history.

(56) References Cited

U.S. PATENT DOCUMENTS

| | | | |
|---|---|---|---|
| 4,939,666 | A | 7/1990 | Hardman |
| 6,188,965 | B1 | 2/2001 | Mayo et al. |
| 6,230,102 | B1 | 5/2001 | Tidor et al. |
| 6,269,312 | B1 | 7/2001 | Mayo et al. |
| 6,490,532 | B1 | 12/2002 | Hogue et al. |
| 8,229,721 | B1 | 7/2012 | Desmet et al. |
| 2001/0032052 | A1 | 10/2001 | Mayo et al. |
| 2001/0039480 | A1 | 11/2001 | Mayo et al. |
| 2002/0004706 | A1 | 1/2002 | Mayo et al. |
| 2011/0245463 | A1 | 10/2011 | Desmet et al. |

FOREIGN PATENT DOCUMENTS

| | | |
|---|---|---|
| WO | WO 98/47089 | 10/1998 |
| WO | PCT/EP00/09460 | 9/2000 |
| WO | WO 01/33438 A2 | 5/2001 |
| WO | WO 01/37147 | 5/2001 |

OTHER PUBLICATIONS

U.S. Appl. No. 10/129,513, filed Nov. 3, 2000, Desmet et al.
U.S. Appl. No. 10/129,516, filed Nov. 3, 2000, Desmet et al.
U.S. Appl. No. 13/020,452, filed Feb. 3, 2011, Desmet et al.
Allen and Mayo, "Dramatic Performance Enhancements for the FASTER Optimization Algorithm," *J. Comput. Chem.* 27:1071-1075 (2006).
Dahiyat et al., "Protein Design Automation," *Protein Science* 5:895-903 (1996).
Dahiyat and Mayo, "De Novo Protein Design: Fully Automated Sequence Selection," *Science* 278:82-87 (1997).
Desmet et al., "Fast and Accurate Side-Chain Topology and Energy Refinement (FASTER) as a New Method for Protein Structure Optimization," *Proteins* 48:31-43 (2002).
Desmet et al., "The Dead-End Elimination Theorem and Its Use in Protein Side-Chain Positioning," *Nature* 356:539-542 (1992).
Desmet et al., "Theoretical and Algorithmical Optimization of the Dead-End Elimination Theorem," *Pac. Symp. Biocomput.* 122-133 (1997).
Gordon and Mayo, "Branch-and-Terminate: A Combinatorial Optimization Algorithm for Protein Design," *Structure* 7:1089-1097 (1999).
Wako and Ishii, "Secondary Structure Prediction of β-subunits of the Gonadotrophin-Thyrotropin Family from Its Aligned Sequences Using Environment-Dependent Amino-Acid Substitution Tables and Conformational Propensities," *Biochemica. et Biophysica. Acta.* 1247:104-112 (1995).
Wernisch et al., "Automatic Proteinc Design with All Atom Force-Fields by Exact and Heuristic Optimization," *J. Mol. Biol.* 301:713-736 (2000).
Milchev et al., "A Monte Carlo Study of Thermodynamic Relaxation in Living Polymers," *J. Phys. II France.* 5:343-347 (1995).
Official Communication for European Patent Application No. 00 984 970.4, dated Oct. 8, 2010.
International Preliminary Examination Report (PCT/EP00/10921), completed Apr. 16, 2002.
International Preliminary Examination Report (PCT/EP00/10923), completed Oct. 17, 2002.
International Search Report (PCT/EP00/10921), mailed Dec. 17, 2001.
International Search Report (PCT/EP00/10923), mailed Mar. 12, 2002.
Office Action (U.S. Appl. No. 10/129,513), mailed Feb. 2, 2005.
Reply to Office Action (U.S. Appl. No. 10/129,513), filed Jun. 1, 2005.
Final Office Action (U.S. Appl. No. 10/129,513), mailed Nov. 7, 2005.
Reply to Final Office Action (U.S. Appl. No. 10/129,513), filed Mar. 7, 2006.
Office Action (U.S. Appl. No. 10/129,513), mailed May 31, 2006.
Reply to Office Action (U.S. Appl. No. 10/129,513), filed Oct. 2, 2006.
Final Office Action (U.S. Appl. No. 10/129,513), mailed Dec. 5, 2006.
Reply to Final Office Action (U.S. Appl. No. 10/129,513), filed Apr. 23, 2007.
Office Action (U.S. Appl. No. 10/129,513), mailed Jul. 11, 2007.
Reply to Office Action (U.S. Appl. No. 10/129,513), filed Nov. 13, 2007.
Office Action (U.S. Appl. No. 10/129,513) mailed Feb. 11, 2008.
Reply to Office Action (U.S. Appl. No. 10/129,513), filed Aug. 11, 2008.
Office Action (U.S. Appl. No. 10/129,513), mailed Dec. 15, 2008.
Reply to Office Action (U.S. Appl. No. 10/129,513), filed Apr. 14, 2009.
Final Office Action (U.S. Appl. No. 10/129,513), mailed Jul. 8, 2009.
Amendment after Final Office Action (U.S. Appl. No. 10/129,513), filed Jul. 26, 2010.

(Continued)

*Primary Examiner* — Anna Skibinsky

(74) *Attorney, Agent, or Firm* — Clark & Elbing LLP

(57) ABSTRACT

The present invention provides methods for generating information related to the molecular structure of a biomolecule.

42 Claims, 13 Drawing Sheets

(56) References Cited

OTHER PUBLICATIONS

Advisory Action (U.S. Appl. No. 10/129,513), mailed Aug. 4, 2010.

Appeal Brief (U.S. Appl. No. 10/129,513), filed Aug. 9, 2010.

Office Action (U.S. Appl. No. 10/129,513), mailed Nov. 4, 2010.

Restriction Requirement (U.S. Appl. No. 10/129,516), mailed Dec. 14, 2007.

Reply to Restriction Requirement (U.S. Appl. No. 10/129,516), filed Jan. 14, 2008.

Office Action (U.S. Appl. No. 10/129,516) mailed Apr. 18, 2008.

Reply to Office Action (U.S. Appl. No. 10/129,516), filed Aug. 21, 2008.

Office Action (U.S. Appl. No. 10/129,516), mailed Jan. 8, 2009.

Reply to Office Action (U.S. Appl. No. 10/129,516), filed May 7, 2009.

Office Action (U.S. Appl. No. 10/129,516), mailed Aug. 14, 2009.

Reply to Office Action (U.S. Appl. No. 10/129,516), filed Jan. 14, 2010.

Final Office Action (U.S. Appl. No. 10/129,516), mailed Mar. 25, 2010.

Reply to Final Office Action (U.S. Appl. No. 10/129,516), filed Jul. 26, 2010.

Extended European Search Report for European Patent Application No. 10179441.0, dated Mar. 4, 2011.

U.S. Appl. No. 13/472,080, filed May 15, 2012, Desmet et al.

Restriction Requirement issued in U.S. Appl. No. 13/020,452, dated Sep. 12, 2012, and pending claims (15 pages).

Brooks et al., "CHARMM: A Program for Macromolecular Energy, Minimization, and Dynamics," *J. Comput. Chem*. 4:187-217, 1983.

Reply to Office Action (U.S. Appl. No. 10/129,513), filed Mar. 3, 2011.

Final Office Action (U.S. Appl. No. 10/129,513), mailed May 25, 2011.

Non-final Office Action (U.S. Appl. No. 10/129,516), mailed Dec. 8, 2011.

Reply to Office Action (U.S. Appl. No. 10/129,516), filed Apr. 6, 2012.

Hydrogen bond, 2012, http://en.wikipedia.org/wiki/Hydrogen_bond.

Molecular dynamics, 2012, http://en.wikipedia.org/wiki/Molecular_dynamics.

Official Communication for European Patent Application No. 10179441.0, dated Apr. 10, 2012 (5 pages).

Non-Final Office Action issued in U.S. Appl. No. 13/020,452, dated Apr. 2, 2013 (16 pages).

Final Office Action issued in U.S. Appl. No. 10/129,516 on Oct. 1, 2012 (21 pages).

```
-- Following residues are modelled
...
Flex(23,ASP)
Flex(24,THR)
Flex(26,ILE)
Flex(27,ARG)
Flex(28,PHE)
Flex(56,THR)
Flex(57,GLU)
Flex(59,VAL)
...
```

FIGURE 2

```
--rotamer library entries for PHE
  TYP  =  PHE
  NRRS =    2
  NSTP =    2       2
  STP  =   10.0    20.0
  NROS =    5
  ROSA =  -66.3    94.3
  ROSA = -179.2    78.9
  ROSA =   66.0    90.7
  ROSA =  -65.0   155.0
  ROSA =  -80.0   200.0
```

FIGURE 7

METHOD FOR GENERATING INFORMATION RELATED TO THE MOLECULAR STRUCTURE OF A BIOMOLECULE

CROSS-REFERENCE TO RELATED APPLICATIONS

This application is a divisional of U.S. application Ser. No. 10/129,516, having a 371(c) date of Apr. 15, 2005, which is the U.S. National Stage of International Application No. PCT/EP00/10921, filed Nov. 3, 2000, which claims the benefit of International Application No. PCT/EP00/09460, filed Sep. 25, 2000, and U.S. Provisional Application No. 60/163,408, filed Nov. 3, 1999.

The present invention relates to the field of structure prediction of biomolecules, in particular to a novel method for generating information related to the molecular structure of a biomolecule, given knowledge of a certain three-dimensional representation of the molecular structure of said biomolecule. This method is therefore applicable within the fields of protein structure analysis, homology modelling, and protein design.

BACKGROUND OF THE INVENTION

The high ratio between the frequency at which new protein sequences become available and the rate of appearance of experimentally determined structures, provides an ideal matrix for the development of homology-based modelling techniques. Homology modelling algorithms basically intend to position new side chains on a backbone taken from a homologous protein with known three-dimensional (3D) structure. When a correct or approximate main-chain structure is not available, for instance in the loop regions of two homologous proteins, it is sometimes possible to generate a set of main-chain structures, position the side chains on each and use some scoring function to select the most probable global structure. This general approach is commonly applied to fields like structure-based homology modelling, the prediction of loop conformations, peptide modelling and protein folding.

From a theoretical point of view, the problem of finding the optimal global arrangement of a set of side chains attached to a particular main-chain structure is a typical combinatorial problem. Not only do side chains interact with the backbone, but their conformation can also be influenced by neighbouring side chains. Yet, F. Eisenmenger et al. in *J. Mol. Biol.* (1993) 231:849-860 found that the majority of side chains can be correctly positioned by taking into account only their interactions with the template: applying this simple template-based method to a test set of 6 proteins, they found that, on average, 53% of all side chains had dihedral angles in agreement with the known structure and that for buried side groups (i.e. having less than 25% exposed accessible surface) this score increased to 74%. When each side chain was modelled in the presence of the complete known structure, the average prediction score increased only to 65% for all side chains and to 84% for the buried side groups. From these observations, the authors concluded that the combinatorial barrier in side-chain positioning hardly exists.

However, several authors tackled the side-chain positioning problem by means of a combinatorial approach or equivalent method. For instance, the Dead-End Elimination (DEE) method takes into account both side-chain/template and side-chain/side-chain interactions and uses a mathematically rigorous criterion to eliminate side-chain rotamers which do not belong to the Global Minimum Energy Conformation (GMEC). Since the elimination routines usually do not yield a unique structure, a combinatorial end stage routine is needed to determine the GMEC.

Other methods, such as Monte Carlo simulation, genetic algorithms, simulated annealing, mean-field optimisation, restricted combinatorial analysis and neural networks, have also been published which, to varying extent, account for side-chain/side-chain combinatorial effects. To date the question of whether the combinatorial barrier in side-chain positioning indeed exists is still unanswered because of the different methods, protein test sets, evaluation criteria and viewpoints in their interpretation used by various authors.

The present inventors, by applying both the Eisenmenger method and the DEE method to a statistically significant test set and by evaluating the results on the basis of all scoring criteria as used by those skilled in the art, could demonstrate that a true combinatorial approach leading to the GMEC, as opposed to the rudimentary Eisenmenger method, yields much better results in terms of potential energy but also that the improvements are much less impressive when considering the number of correctly predicted side-chain conformations. In other words, when using a mathematically rigorous combinatorial method such as the DEE algorithm, one can usually avoid inter-atomic clashes leading to favourable global energies although this is usually accompanied by a gain of only about 10% correctly positioned side chains.

From a practical point of view, the more important question of whether the improved accuracy as obtained by more sophisticated methods effectively balances the extra computational effort cannot be answered in general as it depends on the needs of the user. Yet, an improvement in prediction accuracy at a low computational cost is a long felt need, especially when the side-chain positioning algorithm is to be included as a sub-method in a larger program, e.g. for loop structure prediction, inverse folding, high-throughput homology modelling, etc. There is also a need for a substantial gain in computational speed relative to the DEE method without, if possible, a reduction in accuracy which could be problematic for some of the above-mentioned applications.

While the DEE method is relatively fast for small sets of side chains (<30) and thus useful in applications like flexible docking of peptides or inverse folding, its performance rapidly drops for larger systems.

This, in combination with an urgent need to accelerate protein side-chain computations in different applications, illustrates the need for an alternative method, which preserves the accuracy of the DEE method, especially at the energetical level, but reduces the computational requirements in comparison with the DEE method.

SUMMARY OF THE INVENTION

In one aspect, the present invention provides a method, called the “Fast and Accurate Side-chain Topology and Energy Refinement” (FASTER) method, which is fundamentally different from the DEE method although it can be combined therewith. This method does not necessarily work by eliminating rotamers that are mathematically incompatible with the GMEC. Instead, it operates by selecting a particular starting conformation for each side chain (which is not the case for DEE), followed by gradual optimisation of all side-chain orientations through a number of consecutive and iterative steps. At any time during the FASTER method, a global structure for the system (and its energy) is known, whereas in the DEE algorithm a global structure can only be obtained at the end, if all but one of the rotamers have been eliminated or else if the DEE method is combined with an end stage method such as combinatorial enumeration.

Central to the FASTER method is the repeated application of a perturbation/relaxation/evaluation process to a set of modelled (flexible, rotatable) side chains of a biomolecule, e.g. a set of amino-acid residue portions of a protein. Non-modelled side chains, as well as the main-chain atoms of the biomolecule, are preferably included in a template which is fixed throughout the modelling process. The perturbation step involves the temporary fixation of one or more of the modelled side chains in a selected rotameric state, preferably different from the rotameric state in the current global structure. During the first optimisation round, the current global structure is a first three-dimensional representation of the molecular structure of the biomolecule, whereas in later optimisation rounds, the current global structure is preferably the energetically best global structure found in previous rounds. In the relaxation step, either all or a subset of all side chains other than the perturbed side chain(s) are considered for adaptation to the perturbed side chain(s). This occurs by a local optimisation procedure, preferably in what is known in the art as a batch mode. For each side chain considered for adaptation, the total interaction energy of each rotamer with, on the one hand, the perturbed side chain(s) in their temporarily fixed rotameric state and, on the other hand, the remaining side chains in the rotameric state of the current global structure is calculated, summed and stored in a data structure. From these data, the minimal value is computed for each considered side chain and the accompanying rotameric state is stored as a candidate rotamer to become part of a new global structure. Whether or not these candidate rotamers, together with the temporarily fixed rotamer(s), are accepted and included as part of a new global structure depends on the evaluation step. In this third step, the global energy of the global structure consisting of (i) the template, (ii) the perturbed side chain(s) in a temporarily fixed rotameric state, (iii) the side chains considered for relaxation in their relaxed candidate rotamer state and (iv) the remaining side chains (if any) in their rotameric state of the current global structure, is calculated. This global energy is then compared with the global energy of the current global structure and, if better, the current global structure is preferably discarded and a new global structure is created and stored in a data structure holding the rotameric states as obtained after the perturbation/relaxation steps.

In one optimisation round, the perturbation/relaxation/evaluation process is preferably repeated for all possible single side-chain rotamers, rotamer pairs, triplets and so on, whatever type of optimisation is applicable. Furthermore, different optimisation rounds are preferably performed, until in the last round no global improvement has occurred. Only then, the current global structure resides in a Local Minimum of at least the order x+1, where x is the number of side chains which have been simultaneously perturbed in the perturbation step.

In a first embodiment, the present invention relates to a method for generating information related to the molecular structure of a biomolecule, the method being executable by a computer under the control of a program stored in the computer, and comprising the steps of:

(a) receiving a three-dimensional representation of the molecular structure of said biomolecule, the said representation comprising a first set of residue portions (or side chains) and a template;

(b) modifying the representation of step (a) by at least one optimization cycle; characterized in that each optimization cycle comprises the steps of:

(b1) perturbing a first representation of the molecular structure by modifying the structure of one or more of the first set of residue portions;

(b2) relaxing the perturbed representation by optimizing the structure of one or more of the non-perturbed residue portions of the first set with respect to the one or more perturbed residue portions; and (b3) evaluating the perturbed and relaxed representation of the molecular structure by using an energetic cost function and replacing the first representation by the perturbed and relaxed representation if the latter's global energy is more optimal than that of the first representation; and (c) terminating the optimization process according to step (b) when a predetermined termination criterion is reached; and (d) outputting to a storage medium or to a consecutive method a data structure comprising information extracted from step (b).

The method of this first embodiment may further comprise providing, prior to step (b):

a set of structural variation rules, e.g. including a rotamer library, for the first set of residue portions and performing any modification in step (b) in accordance with the said set of structural variation rules, and/or a set of structural compatibility rules, e.g. according with the computation of intramolecular interactions using an energetic cost function (for instance allowing to calculate a quantitative estimate of the potential or free energy of any global structure of the biomolecule or of any set of residue portions thereof), and performing any relaxation step (b2) in accordance with the said set of structural compatibility rules.

In a second embodiment, the present invention relates to a method for generating a model of the molecular structure of a biomolecule and information related to the said molecular structure, the method being executable by a computer under the control of a program stored in the computer, and comprising the steps of (a) receiving a representation of a complete or partial molecular structure of said biomolecule comprising a plurality of residue portions and optionally completing the partial molecular structure using biochemical rules, and forming from the plurality of residue portions a first set of residue portions, the remainder of the molecular structure being designated as a template;

(b) defining an energetic cost function which assigns a quantitative energetic cost to any global structure of the said biomolecule and to any set of residue portions thereof;

(c) providing a set of rotamers for each residue portion of the first set of residue portions formed in step (a);

(d) assigning one rotamer from the set of rotamers of step (c) to each residue portion of the first set formed in step (a), thereby defining a current global structure for said biomolecule;

characterized in that the method further comprises modifying said current global structure through an optimization process comprising at least one optimization cycle, wherein each optimization cycle comprises:

(e) a perturbation step including providing, from the first set of residue portions of step (a):

a second set of perturbed residue portions containing one or more residue portions each in a temporarily fixed rotameric state selected from the set of rotamers of step (c), and a third set of residue portions containing one or more of the non-perturbed residue portions of the first set in their assigned rotameric state;

(f) relaxing each residue portion of the third set towards a more optimal state by considering at least some of the rotamers of the set of step (c) and calculating, for each considered rotamer, while using the energetic cost function of step (b), its individual contribution to the global cost of the system consisting of the template, the one or more perturbed residue portions of the second set in their fixed rotameric states, the residue portion of the third set being considered for relaxation in its considered rotameric state and the remaining residue portions of the first set in their assigned rotameric states, and selecting from the set of considered rotamers one rotamer in accordance with the calculated individual contributions;

(g) calculating, using the energetic cost function of step (b), the global cost of the system consisting of the template, the one or more perturbed residue portions of the second set in their fixed rotameric states, the one or more residue portions of the third set in their rotameric states selected in step (f) and the remaining residue portions of the first set in their assigned rotameric states;

(h) establishing a first acceptance criterion by way of comparing the global cost calculated in step (g) with the global cost, calculated using the energetic cost function of step (b), of the current global structure and, if said first acceptance criterion is met, assigning by way of replacement, for each perturbed residue portion of the second set, the currently assigned rotamer with the rotamer fixed in step (e) and, for each residue portion of the third set, the currently assigned rotamer with the rotamer selected in step (f), thereby defining a new current global structure;

and wherein the method further comprises:

(i) a termination step including terminating the optimization process as soon as a predetermined termination criterion is reached; and (j) a data outputting step including outputting to a storage medium or to a consecutive method a data structure comprising information extracted from a current global structure defined in step (h).

For instance, the information outputted in step (j) may be a global or partial representation of the three-dimensional structure of a biomolecule, or the global cost of a global structure calculated in step (g). The data structure outputted in step (j) may comprise a set of data extracted from the calculations in step (f), being useful e.g. to assess a global structure wherein one or more residue portions have undergone the perturbation step (e) and one or more other residue portions have been relaxed in step (f).

In both embodiments of the method of the invention, the number of residue portions in the first set present in step (a) is preferably at least 5.

As will be appreciated by those skilled in the art, the FASTER method can be implemented in many ways. Possible variations include, but are not limited to, variations in the definition of the template, the nature of the modelled biomolecule, the number and type of the modelled side chains, the rotamer library, the energetic cost function, the selection of perturbed and relaxed side chains, the order in which side chains are perturbed and relaxed, relaxation in batch versus gradual mode, the acceptance and termination criteria, the content of the data structure, as well as possible combinations with other methods. Still, a common feature of all possible variations is that any implementation of the present invention should include, at least one or more perturbation/relaxation/evaluation cycles that are applied to the side chains of a biomolecule.

We demonstrate hereinafter that the basic perturbation/relaxation/evaluation cycle is responsible for both the high performance and high quality of results of the method. In other words, the best conformation of an individual side chain cannot be obtained by simply selecting its energetically most optimal conformation within the context of a global structure, except if that global structure is the correct structure for the biomolecule, which is generally not the case during a search process. Consequently, a simple local optimisation of individual side chains should lead to sub-optimal global results, and this is confirmed by experimental evidence provided in the following EXPERIMENTAL SECTION. Indeed, local optimisation is basically what is performed in pass 1 of the FASTER method in its preferred embodiment and, although pass 1 is useful as a preparative step, the results obtained are qualitatively unsufficient. The combination of the three individual steps (in passes 3 and 4 of the preferred FASTER embodiment) drastically increases the quality of results.

Passes 3 and 4 of the preferred embodiment of the FASTER method exploit the full power of the perturbation/relaxation/evaluation approach in optimising the 3D-structure of biomolecules, preferably proteins. A systematic comparison between FASTER and DEE-modelled proteins has shown that the molecular structures obtained by the FASTER method are extremely close to the GMEC both in terms of side-chain score and global energy. For example, the FASTER method succeeds in approximating the global minimum to about 0.5 kcal $mol^{-1}$ for a medium-sized protein containing 200 rotatable side groups. Importantly, when both methods produce virtually identical results, the FASTER method is 100 to 1000 times faster than the DEE method.

In an embodiment of the present invention, the FASTER method provides significant information about the conformational flexibility of individual side chains. It has been found that strictly rigid side chains are concentrated mainly in the core, while very flexible side chains are found almost exclusively among solvent-oriented residues. From a practical point of view, an important feature of the FASTER method is the unprecedented combination of an extremely high computational speed with near-optimal prediction accuracy. This favourable combination implies that the FASTER method is probably an ideal side-chain positioning method to be incorporated within advanced protein modelling applications such as high-throughput homology modelling, loop structure prediction, inverse folding, protein design and the like.

In addition, the FASTER method opens a new gateway to the field of protein design. By a minor modification of the preferred embodiment, fully consistent with the perturbation/relaxation/evaluation cycle, the FASTER method can be used to predict the mutability of individual side chains. More specifically by executing in the perturbation step not only conformational changes but also changes in the side-chain type, the FASTER method can generate a quantitative estimate of the energetic cost to substitute a wild type side chain into a side chain of another type. Hence, it is possible to generate, for a complete or partial biomolecule, a data structure containing energetic values which can be interpreted as mutability indices: the higher the energetic cost of a given mutation, the less probable this mutation may be or, alternatively, the less stable a biomolecule comprising this mutation may be. Such mutability data structures can be compiled for single as well as for pairs (or multiplets) of residues. Whereas the former data structures reflect the energetic cost of point mutations, the pairwise mutability indices can be used to assess, for example, the effects of multiple, combined substitutions.

For this purpose it is, in essence, sufficient to extend the conventional definition of a rotamer from a pure conformational description to a description which defines both the side chain structure and its type. In other words, different rotamers considered at a specific position in a biomolecule may also consist of different side chain types. This concept of generalised rotamers was first introduced by Dahiyat et al. in *Protein Sci* (1996) 5:895-903 in the context of protein design. For an optimal performance of the FASTER method with respect to protein design, some modifications of the standard "conformational" version are preferred, as explained in the section USE OF THE FASTER METHOD FOR PROTEIN DESIGN.

In any of the methods of the present invention the biomolecule may be a protein, a polypeptide, a polynucleotide, a polysaccharide or a complex comprising at least one biologically-active macro-molecule.

In addition, this invention relates to a method comprising the steps of:

(a) inputting a description of a molecular structure of a biomolecule consisting of a plurality, of residue portions at a near location;

(b) transmitting the description to a remote processing engine; and (c) receiving, at the near location from the remote processing engine, a three dimensional representation generated by the FASTER method as above-defined.

This invention also relates to:

- a data structure representing a biomolecular structure generated by the FASTER method as above-defined, for instance in the form of a protein sequence which is different (preferably at least 10% different, more preferably at least 25% different, most preferably at least 50% different) from any known protein sequence.
- a nucleic acid sequence encoding a protein sequence generated by the FASTER method as above-defined.
- an expression vector or a host cell comprising the nucleic acid sequence as above-defined.
- a pharmaceutical composition comprising a therapeutically effective amount of a protein sequence generated by the FASTER method (as above-defined) and a pharmaceutically acceptable carrier.
- a method of treating a disease in a mammal, comprising administering to said mammal a pharmaceutical composition such as above-defined.

The present invention, its characteristics and embodiments, will now be described with reference to the following drawings and detailed description.

BRIEF DESCRIPTION OF THE DRAWINGS

FIG. 2 shows a possible fragment of a script serving as the input source for the method of this invention and defining which residue types need to be positioned at which positions in the protein. In this example, the first line is a comment line, the term "Flex" is a command for the method implemented as an executable program to store the arguments as flexible residue properties, where the first argument is the residue position and the second argument is the side-chain type. The precise format of this data source is irrelevant within the context of the method of this invention.

FIG. 7 illustrates a rotamer library used for PHE in the following DEE and FASTER comparison experiments, wherein TYP=amino acid side-chain type; NRRS=number of dihedral angles in the side chain; NSTP=number of steps to be taken around standard dihedral angle values; STP=step size for each dihedral angle in degrees; NROS=number of rotamers for the current side-chain type; ROSA=dihedral angle value for each dihedral angle in degrees. The steps mentioned above serve to extend the standard rotamer library in a systematic way. In this example, two steps are taken around dihedral angle $\chi_1$ as well as around $\chi_2$, where "around" means above and below the standard value and where steps around different dihedral angles are to be combined. For example, the first rotamer has standard torsion angles of −66.3° and 94.3° for $\chi_1$ and $\chi_2$, respectively. Given the 2 steps on $\chi_1$ and $\chi_2$ this leads to 25 rotamers after expansion, i.e. the standard value for $\chi_1$ (−66.3° augmented with −2×10°, −1×10°, 0×10°, 1×10° and 2×10°, combined with the standard value for $\chi_2$ (94.3° augmented with −2×20°, −1×20°, 0×20°, 1×20° and 2×20°. Thus 5 standard rotamers result in 5×25=125 rotamers in the extended library which is used in all experiments described.

Figure 1:
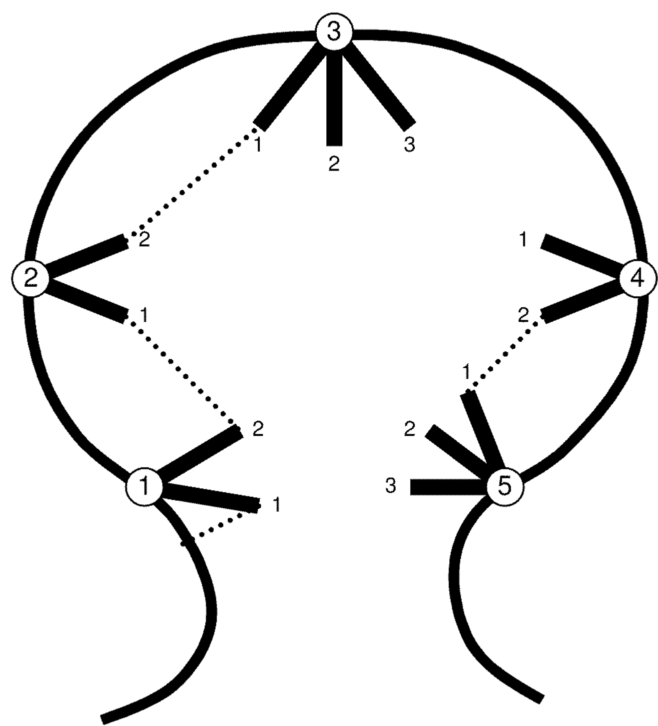
FIG. 1 is a schematic representation of a hypothetical protein fragment, where the exterior line symbolises the backbone, and the short bold lines denote different rotameric conformations of the side chains. Dotted lines show energetically unfavourable side-chain interactions either with the backbone (e.g. residue 1, rotamer 1) or with another side chain (e.g. residue 1, rotamer 2 with residue 2, rotamer 1). The combinatorial problem can be inferred from this picture as the calculation method must detect global solutions where at least all unfavourable interactions are avoided. On the other hand, this figure also illustrates that the combinatorial search process can be facilitated by exploiting local atomic conflicts (e.g. residue 1, rotamer 1 is prohibited which forces it into rotamer 2, which in turn forces residue 2 into rotamer 2 due to a prohibitive interaction with the rotamer 1; the same mechanism is responsible for pushing residue 3 into rotamers 2 or 3). In the same sense, favourable interactions (not shown) can exert a dominant driving force. As a conclusion the GMEC can be obtained from the enumeration of all possible non-prohibited rotamer combinations, but also a particular search path might exist which rapidly relaxes the system by avoiding local conflicts and/or promoting locally favourable interactions.

Computer 10 also includes a graphical user interface that resides within a machine-readable media to direct the operation of computer 10. Any suitable machine-readable media may retain the graphical user interface, such as a random access memory (RAM) 24, a read-only memory (ROM) 26, a magnetic diskette, magnetic tape, or optical disk (the last three being located in disk and tape drives 23). Any suitable operating system and associated graphical user interface (e.g., Microsoft Windows) may direct CPU 15. In addition, computer 10 includes a control program 51 which resides within computer memory storage 52. Control program 51 contains instructions that when executed on CPU 15 carries out the operations described with respect to the methods of the present invention as described herein.

TABLE 1

| PDB code | NSC | Description |
|---|---|---|
| 1AKZ | 177 | URACIL-DNA GLYCOSYLASE |
| 1AMM | 143 | GAMMA B-CRYSTALLIN |
| 1AMP | 225 | AMINOPEPTIDASE |
| 1ARB | 183 | ACHROMOBACTER PROTEASE I |
| 1BEC | 183 | T CELL ANTIGEN RECEPTOR |
| 1CEM | 276 | CELLULASE CELA |
| 1CHD | 141 | CHEB METHYLESTERASE |

TABLE 1-continued

| PDB code | NSC | Description |
|---|---|---|
| 1CNV | 221 | CONCANAVALIN B |
| 1CVL | 234 | TRIACYLGLYCEROL HYDROLASE |
| 1DIN | 161 | DIENELACTONE HYDROLASE |
| 1DTS | 158 | DETHIOBIOTIN SYNTHASE |
| 1EDG | 308 | ENDOGLUCANASE A |
| 1GND | 347 | GUANINE NUCLEOTIDE DISSOCIATION INHIBITOR |
| 1HBQ | 140 | RETINOL BINDING PROTEIN |
| 1IAE | 164 | ASTACIN |
| 1ILK | 129 | INTERLEUKIN-10 |
| 1JCV | 108 | CU/ZN SUPEROXIDE DISMUTASE |
| 1JER | 89 | CUCUMBER STELLACYANIN |
| 1L68 | 131 | LYSOZYME MUTANT |
| 1LBU | 138 | MURAMOYL-PENTAPEPTIDE CARBOXYPEPTIDASE |
| 1LIT | 104 | LITHOSTATHINE |
| 1MLA | 205 | MALONYL-COENZYME A ACYL CARRIER PROTEIN |
| 1MML | 194 | MMLV REVERSE TRANSCRIPTASE |
| 1NAR | 244 | NARBONIN |
| 1NIF | 248 | NITRITE REDUCTASE |
| 1OMP | 276 | D-MALTODEXTRIN-BINDING PROTEIN |
| 1PMI | 353 | PHOSPHOMANNOSE ISOMERASE |
| 1RBU | 119 | RIBONUCLEASE H MUTANT |
| 1RIE | 95 | RIESKE IRON-SULFUR PROTEIN |
| 1SGT | 148 | TRYPSIN |
| 1TFE | 115 | ELONGATION FACTOR TS |
| 1THV | 139 | THAUMATIN ISOFORM A |

TABLE 2

| | Score Ident.$^{(a)}$ (%) | Score Vol.$^{(b)}$ (%) | $\Delta E^{(c)}$ (kcal mol$^{-1}$ res$^{-1}$) |
|---|---|---|---|
| Start | 57.8 ± 5.8 | 75.2 ± 4.5 | $(1.5 \pm 9.0) \times 10^{14}$ |
| Pass 1 | 76.2 ± 5.0 | 85.1 ± 3.9 | $(2.9 \pm 13.7) \times 10^{7}$ |
| Pass 2 | 83.0 ± 5.3 | 90.0 ± 3.7 | 0.13 ± 0.09 |
| Pass 3 | 96.1 ± 3.9 | 97.7 ± 2.8 | 0.008 ± 0.015 |
| Pass 4 | 98.2 ± 3.4 | 98.9 ± 2.2 | 0.002 ± 0.011 |

Table 2 shows a comparison of the FASTER-modelled protein structures with the same proteins in the GMEC structure (as computed by the DEE algorithm). All values are averaged over the 50 proteins in the test set. Averaged values as well as standard deviations are given for the starting structure and after each pass of the FASTER method. (a)=average percentage of identical rotamers after FASTER and DEE modelling; (b)=average percentage side chains with a volume overlap >70%; (c)=difference in E_TOTAL per residue, expressed in kcal mol$^{-1}$ res$^{-1}$

TABLE 3

| | DEE | | 4-pass FASTER | | 3-pass FASTER | | start | |
|---|---|---|---|---|---|---|---|---|
| Criterion | <25% | all | <25% | all | <25% | all | <25% | all |
| RMSD (Å) | 1.02 ± 0.19 | 1.55 ± 0.22 | 1.01 ± 0.18 | 1.54 ± 0.21 | 1.02 ± 0.17 | 1.54 ± 0.20 | 1.37 ± 0.22 | 1.83 ± 0.21 |
| 70% vol. | 85.2 ± 5.1 | 71.3 ± 6.0 | 85.3 ± 4.8 | 71.4 ± 5.7 | 85.1 ± 4.4 | 71.4 ± 5.8 | 77.0 ± 5.5 | 63.9 ± 5.6 |
| $\chi_{1,2} \pm 40°$ | 84.2 ± 5.7 | 71.3 ± 5.9 | 84.5 ± 5.5 | 71.4 ± 5.8 | 84.2 ± 5.2 | 71.3 ± 5.9 | 75.8 ± 5.5 | 63.6 ± 5.2 |

TABLE 1-continued

| PDB code | NSC | Description |
|---|---|---|
| 1THX | 89 | THIOREDOXIN |
| 1VHH | 126 | SONIC HEDGEHOG |
| 1WBA | 135 | WINGED BEAN ALBUMIN 1 |
| 1WHI | 95 | RIBOSOMAL PROTEIN L14 |
| 1XJO | 188 | AMINOPEPTIDASE |
| 1XNB | 145 | XYLANASE |
| 1ZIA | 85 | PSEUDOAZURIN |
| 2CPL | 122 | CYCLOPHILIN A |
| 2CTC | 252 | CARBOXYPEPTIDASE A |
| 2DRI | 201 | D-RIBOSE-BINDING PROTEIN |
| 2END | 112 | ENDONUCLEASE V |
| 2ENG | 134 | ENDOGLUCANASE V |
| 2HFT | 177 | HUMAN TISSUE FACTOR |
| 2PRK | 199 | PROTEINASE K |
| 2SIL | 313 | SIALIDASE |
| 3PTE | 270 | D-ALANYL-D-ALANINE CARBOXYPEPTIDASE/ TRANSPEPTIDASE |
| 8ABP | 229 | L-*ARABINOSE-BINDING PROTEIN MUTANT |
| 9PAP | 153 | PAPAIN |

Table 1 lists the 50 protein structures used in the DEE and FASTER experiments, wherein NSC is the number of flexibly treated side chains in the molecule.

Table 3 shows analyses of the modelled proteins in comparison with the X-ray determined structures. Three evaluation methods have been used, i.e. (i) the difference in atomic positions as measured by the RMSD (in Angstrom) of the side-chain atoms (including $C_\beta$), (ii) the 70% volume overlap criterion and (iii) the $x_{1,2}$ test where a side chain is assumed to be correctly placed if both $\chi_1$ and $\chi_2$ are within 40° of the dihedral angle observed in the X-ray structure. The values are averaged over all proteins in the test set and standard deviations are given. This analysis was done for DEE, 4-pass FASTER and 3-pass FASTER modelled structures as well as for the Eisenmenger starting structure. Separate analyses were performed for the buried side chains (less than 25% accessible surface area) and for all side chains in a molecule.

Glossary

Throughout the foregoing and following description of the invention, the abbreviations, acronyms and technical terms used shall have the following meaning and definition:

Abbreviations:

ALA, ARG, ASN, ASP, CYS, GLN, GLU, GLY, HIS, ILE, LEU, LYS, MET, PHE, PRO, SER, THR, TRP, TYR, VAL: standard 3-letter code for the naturally occurring amino acids (or residues) named, respectively: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine.

ASA: Accessible Surface Area
ciBR: Conditional Iterative Batch Relaxation
dPR: Double-residue Perturbation/Relaxation
DEE: Dead-End Elimination
FASTER: Fast and Accurate Side-chain Topology and Energy Refinement
GMEC: Global Minimum Energy Conformation
iBR: Iterative Batch Relaxation
IMEC: Intermediate Minimum Energy Conformation
PDB: Protein Data Bank
RMSD: Root-Mean-Square Deviation
sPR: Single-residue Perturbation/Relaxation Technical Terms:

Accessible Surface Area
: The surface area of (part of) a molecular structure, traced out by the mid-point of a probe sphere of radius ~1.4 Å rolling over the surface.

Amino Acid, Amino Acid Residue
: Group of covalently bonded atoms for which the chemical formula can be written as $^{+}H_3N$—CHR—$COO^{-}$, where R is the side group of atoms characterizing the amino acid type. The central carbon atom in the main-chain portion of an amino acid is called the alpha-carbon ($C_\alpha$). The first carbon atom of a side chain, covalently attached to the alpha-carbon, if any, is called the beta-carbon ($C_\beta$). An amino acid residue is an amino acid comprised in a chain composed of multiple residues and which can be written as —HN—CHR—CO—.

Backbone
: See: Main chain

Batch Mode
: A specific mode of modifying a system composed of different individual parts. First the system is in an initial global state where each part is assigned a well-defined individual state. Next, the system is modified through a series of actions where, in each action, only one individual part is changed. When performing any of these individual modifications, the remainder of the system is considered in the same initial global state. Thus, any previous change must either be undone, or a new change must depart from said initial global state.

Conformational Space
: The multidimensional space formed by considering (the combination of) all possible conformational degrees of freedom of a biomolecule, where one degree of freedom usually refers to the torsional rotation around a single covalent bond. In a broader sense, it also includes possible sequence variation by extending the definition of a rotamer to a particular amino acid type in a discrete conformation.

Dead-End Elimination, DEE
: A method to reduce the conformational space of a side-chain modelling task by eliminating individual side-chain rotamers which are incompatible with the system on the basis of one or more rigorous mathematical criteria. By a variant of this method, pairs of rotamers belonging to different residues can also be eliminated.

Dihedral Angle, Torsional Angle
: 1. A particular single covalent bond in a molecule, susceptible to torsional rotation (e.g. a TRP side chain has two dihedral angles, commonly referred to as $\chi_1$ and $\chi_2$). 2. The value for a dihedral angle in the first sense, according to certain IUPAC conventions (e.g. $\chi_1$=59.2 degrees for a given TRP residue in a given molecular structure of a protein).

Eisenmenger Structure
: The global structure of a biomolecule for which all rotatable side chains have been placed in the rotameric state displaying the minimal rotamer/template interaction energy, given the template, the energy function and the rotamer library used.

Energy Function, Force Field
: The function, depending on the atomic positions and chemical bonds of a molecule, which allows to obtain a quantitative estimate of the latter's potential or free energy.

Environment Energy
: The total energy of a rotamer in a given environment of assigned side-chain rotamers, e.g. an IMEC, as calculated according to equation 1.

Flexibility Coefficient
: The fraction of rotamers known in the rotamer library for side chain i which are energetically compatible with the molecular structure of the biomolecule. It may be computed according to equation 7.

Flexible Side Chain, Rotatable Side Chain, Modelled Side Chain
: A side chain modelled during performance of the FASTER method. Importantly, this a priori flexibility is not to be confused with the degree of flexibility derived from the computed flexibility coefficients, which reflects the true, energetically allowed flexibility of a side chain in the biomolecule.

Global Energy
: The total energy of a global structure (e.g. an IMEC or the GMEC) which may be calculated in accordance with the applied energy function. Equation 3 provides a means to compute the global energy of a particular IMEC.

Global Minimum
: The globally optimal solution of a biomolecule (e.g. a protein) consisting of a number of elements (e.g. residue positions) which are a priori susceptible to variation (e.g. using the concept of rotamers).

Global Minimum Energy Conformation, GMEC
: The global conformation of a biomolecule which has the lowest possible global energy according to the applied energy function, rotamer library and template structure.

Global Structure, Global Conformation
: The molecular structure of a uniquely defined biomolecule, e.g. represented as a set of cartesian co-ordinates for all atoms of the biomolecule.

Homology Modelling
: The prediction of the molecular structure of a biomolecule (e.g. a protein) on the basis of a template structure.

Intermediate Minimum-Energy Conformation, IMEC
: The global structure of a biomolecule at some intermediate step during the FASTER process. Its properties are (i) the assignment of a unique rotamer to each rotatable side chain, (ii) the specific notation as a set of indices on the rotamer library, (iii) its inconstancy due to frequent updates in different iteration cycles. An IMEC is opposed to the GMEC as it generally does not correspond with the global minimum, except in the last stages of the FASTER process.

Local Minimum
: A global state of a biomolecule consisting of e.g. a template and a set of rotatable side chains, wherein any change in the rotameric state(s) of any side chain(s) leads to a global state having a worse global energy according to the applied energy function. For a local minimum of the $n^{th}$ order, any simultaneous change of n side chain always leads to a worse situation, i.e. a higher energy.

The GMEC is a minimum of the $N^{th}$ order, where N is the number of involved side chains.

Main Chain, Backbone

The part of a biomolecule consisting of one or more near-linear chains of covalently bonded atoms, which can be written as (—NH—CH(–)-CO—)$_n$. Herein, the $C_\beta$-atom is considered as a pseudo-backbone atom and is included in the template because its atomic position is unambiguously defined by the positions of the true backbone atoms.

Perturbation (Sub-)Step,

The first sub-step of the basic optimization cycle of the FASTER method. Performing the perturbation of an IMEC can be interpreted as the temporary modification (and virtual fixation) of one or more individual side-chain conformations.

Perturbation Energy

The change in global energy accompanying the change in global structure from a first state, being the GMEC (or a good approximation thereof), to a second state constructed by the perturbation of a single (or pair of) rotatable side chain(s) from said first state, followed by the global relaxation of the other side chains. It may be calculated according to equation 6.

Protein Data Bank

The single international repository for the processing and distribution of 3-D macromolecular structure data primarily determined experimentally by X-ray crystallography and nuclear magnetic resonance.

Protein Design

That part of molecular modelling which aims at creating protein molecules with altered/improved properties like stability, immunogenicity, solubility and so on.

Relaxation, Adaptation

The second sub-step of the basic optimization cycle of the FASTER method. Its performance essentially involves testing each non-perturbed side chain for the presence of a particular rotameric state which leads, together with the perturbed side chain, to a better global situation.

Root-Mean-Square Deviation, RMSD

The average quadratic deviation between the atomic positions, stored in two sets of co-ordinates, for a collection of atoms.

Rotamer, Rotameric State

An unambiguous discrete structural description of an amino acid side chain, whether preferred or not. According to this definition, which is extended over the usual definitions by considering less preferred states, it is not required that rotamers be interchangeable via rotation only.

Rotamer Library

A table or file comprising the necessary and sufficient data to define a collection of rotamers for different amino acid types.

Rotamer/Template (Interaction) Energy

The sum of all atomic interactions, as calculated using the applied energy function, both within a given side-chain rotamer at a specific position in a biomolecule structure and between the rotamer and the template.

Sequence Space

The multidimensional space formed by considering the combination of all (or a set of) possible amino acid substitutions at all (or a set of) residue positions in a biomolecule.

Side Chain, Side Group

Group of covalently bonded atoms, attached to the main chain portion of an amino acid (residue).

Side-Chain/Side-Chain Pair(Wise) (Interaction) Energy

The sum of all atomic interactions, as calculated using the applied energy function, between two side-chain rotamers at two specific positions in a biomolecule structure.

Standard Geometry

A set of standard reference values for bond lengths, bond angles and planarity parameters which are interrelated with the applied energy function since they correspond to the minimal energy contributions in the molecular structure of a biomolecule.

Steepest Descent Energy Minimization

Simple energy minimization method, belonging to the class of gradient methods, only requiring the evaluation, performed in accordance with a particular energy function, of the potential energy and the forces (gradient) of a molecular structure.

Template

All atoms in a modelled biomolecule structure, except those of the rotatable side chains.

DETAILED DESCRIPTION OF THE INVENTION

The present invention concerns the quantitative prediction of the atomic co-ordinates of biomolecules, especially protein side-chain atoms, given knowledge of the co-ordinates of the main-chain atoms. This prediction occurs by the performance of the FASTER method, the name of which reflects its most important features, i.e. the method (i) is inherently fast compared to other methods producing equivalent results, (ii) produces accurate results identical with or very close to the global minimum of the system, (iii) is suited to model the topology of protein side-chain atoms by searching for their energetically optimal conformation.

One aspect of the method is to iteratively optimise a global structure by repeatedly applying a series of perturbation/relaxation/evaluation steps. In each such step, a number of side chains are temporarily fixed (perturbed) and the other side chains are given the possibility to adapt to this situation (relaxation). If such operation results in a better global structure (after evaluation), the latter can be accepted as a whole and the previous structure is replaced by the new one. Said adaptation of side chains preferably occurs in batch mode (as opposed to gradual adaptation), meaning that a global conformational update is performed only after considering all side chains within the fixed context of the previously accepted structure, but the present invention is not limited thereto. The iterative nature of the method resides in the fact that the perturbation/relaxation/evaluation steps are preferably repeated until a predefined termination criterion is met (e.g. convergence to a unique, constant structure). In order to achieve an optimal computational speed, it is preferred to apply the whole process of iterative optimisation while using different execution parameters, as described below.

In a preferred embodiment of the invention, the FASTER method combines four different variants, called “passes”, of the basic iterative perturbation/relaxation/evaluation cycle. These variants are characterised by specific settings of user-defined execution parameters, in order to enable/disable the perturbation and evaluation sub-steps and to individually enable/disable the relaxation of side chains. In a preferred embodiment, the FASTER method consists of two preparative passes (1 and 2) which remove the most obvious local constraints, followed by two passes (3 and 4) which are more effective in avoiding complex local minima. In passes 1 and 2 both the perturbation and evaluation sub-steps are switched off, whereas in passes 3 and 4 all sub-steps are enabled. The difference between passes 1 and 2 is that in the former, all side chains are unconditionally relaxed, whereas in the latter side chains to be relaxed are selected on a random basis. Pass 4 differs from pass 3 mainly in the number of side chains that are perturbed simultaneously during one step: in pass 3 only single side chains are perturbed while in pass 4 perturbations occur by temporarily fixing the conformation of side chain pairs. For an optimal performance, passes 1-4 are executed in consecutive order, the output structure (and corresponding global energy) resulting from one pass serving as the input structure for the next pass. The method requires a starting structure which from a logical perspective is preferably set identical to the Eisenmenger structure, being a fair compromise between a fast computation and an acceptable initial accuracy. In the end, the method yields a final structure which can be further analysed and/or refined by conventional modelling methods. This method, including passes 1-4, may be preceded by some rotamer elimination steps (e.g. DEE) in order to reduce the number of side-chain rotamers to be taken into account during the perturbation and relaxation steps. Yet, such pre-elimination of rotamers may have only a marginal effect on the performance of the method and is considered a non-essential step of the present invention. In order to function properly, the method requires (i) an appropriate description of a protein main-chain structure, (ii) a list of residue positions in the main chain to be considered, (iii) a list of side-chain types to be modelled at said residue positions, (iv) an appropriate side-chain rotamer library and (v) a useful energetic function.

The FASTER method fundamentally differs from the Monte Carlo simulation method in many respects: (i) one iteration step consists of a combination of local perturbation with global relaxation in rotameric space, (ii) the selection of side chains to be perturbed occurs systematically instead of randomly and (iii) the acceptance of a new global structure is not probabilistic but is that its energy is better than the energy before perturbation. Moreover the specific combination of the key-elements of the method (local perturbation, global relaxation and energetic downhill movement) provides a new solution to the problem of avoiding local minima. Whenever the biomolecule system encounters a local minimum, the different perturbation/relaxation steps systematically attempt to escape from this minimum towards another minimum with lower energy, thus, from an energetic perspective, towards the global minimum.

The FASTER method can be embodied in an executable program, hereafter called the FASTER method, program or algorithm, which may be implemented on a general purpose or dedicated computer system. In the following detailed description of the different parts of the FASTER method, all variable names, array and object names, parameters and memory storage methods are considered as trivial programming aspects and are susceptible to alterations in various implementations of the method, as will be appreciated by those skilled in the art. In the following description, the word "algorithm" should be understood as the concrete embodiment of the method on which it is based. Consequently, the terms "algorithm", "method" and "program" are in principle interchangeable although the term "algorithm" is preferably used when minor programming variations, consistent with the method, are present.

Input Data

In general, the FASTER algorithm uses four main sources of input data. The first is the atomic co-ordinates of a main chain (backbone) of a protein molecule that is assumed to be structurally homologous, i.e. similar in 3D-structure to the protein molecule that is treated by the method. Alternatively, if available, the atomic co-ordinates of a full protein, i.e. main chain, side chains and possibly occurring ligands can be provided. Another possibility is a computationally generated backbone structure including, but not limited to, a backbone structure created by torsional rotation around the main-chain dihedral angles $\phi$ and $\psi$. In the definition of the protein, there are no limits to the length of the chain (provided that at least two amino acids are linked together) or to the number of chains. Also included in the definition of the protein may be domains (e.g. functional, enzymatic or binding domains) as well as smaller fragments such as turns or loops. By extension, the method may also be applied to molecules such as peptides, peptido-mimetic structures, peptoids, and even organic molecules, as long as the 3D-structure of a covalently linked chain of atoms can be retrieved or computer-generated having at least two single non-crosslinked side groups.

Second, the algorithm requires a list of side chains as well as the amino acid residue positions on the main chain at which the side chains are to be positioned (see FIG. 2), hereafter called flexible or rotatable side chains. The remainder of the molecular structure, i.e. all atoms except those of the flexible side chains, preferably including also $C_\beta$ atoms, is hereafter called the template. The list of flexible residues can contain all the amino acid residues of the protein or any possible subset thereof. It can also contain any mixture of original and non-original side-chain types, further called native and non-native types, respectively. When non-peptidic side groups are provided, either the program should be able to recognise them (i.e. to link their name to an internal description of the required atomic properties such as chemical type, bond lengths and angles) or these data may be provided in the input file and the program is able to process this information so as to generate the side groups in standard geometry.

Third, the algorithm must have access to a library describing sterically acceptable side-chain 3D-structures (hereafter called rotamers) called the rotamer library. In a preferred embodiment, the rotamer library is stored on a computer readable data carrier such as a disk to which the algorithm has access, although the library can also be provided by the user or generated by an algorithm on the basis of known physico-chemical principles such as the known physico-chemical properties of amino acid residue types. The rotamer library must provide unambiguous, representative rotameric descriptions for at least those flexible side chains being provided. A rotameric description is preferably, but not necessarily, presented as a list of torsional angle values for all chemical bonds within a particular side-chain type and for the chemical bond that connects it to the template. In case of two connections with the template (e.g. for a PRO side chain), a torsion angle value for one of them is sufficient. Any rotameric description in the rotamer library must provide the necessary and sufficient information for the program to be able to construct the atomic co-ordinates of the corresponding side group in a well-defined conformation onto the template.

Fourth, the algorithm must have access to a minimal set of parameters for each atom type in conjunction with a minimal set of equations describing pairwise atomic interactions, hereafter called Energy Function or force field. The set of parameters and force field equations must be such that for any full 3D-structure of the biomolecule, or any fragment thereof, or any pair of fragments, a representative estimation of the potential energy can be made within a reasonable period of computing time. In addition, the force field, including the parameters, must be such that the total energy of any global structure (composed of the template and the flexible side chains adopting each a specific rotameric conformation) can be computed or at least quantitatively estimated on the basis of equation 3. The most frequently used energy functions have been reviewed by Gordon et al. in *Structure* (1999) 7:1089-1098.

Initialisations

Figure 3:
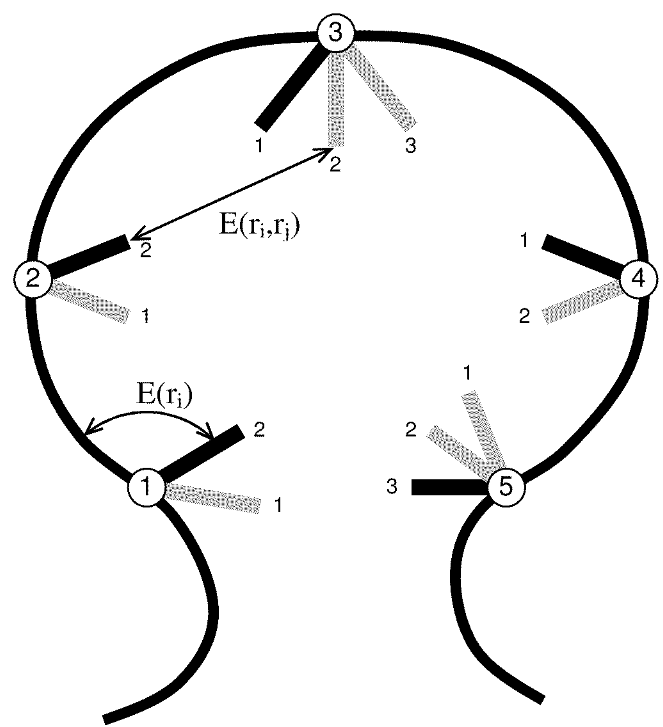
FIG. 3 illustrates the meaning of two basic types of energy terms as used in an embodiment of the present invention. The rotamer/template interaction energies $E(r_i)$ include all atomic interactions within the rotamers $r_i$ and between the rotamers $r_i$ and the template. For example, the two-headed arrow labelled as such is the rotamer/template energy for rotamer r=2 of side chain i=1. The side-chain/side-chain pairwise energies $E(r_i, r_j)$ include all atomic interactions between rotamers $r_i$ and $r_j$. The two-headed arrow labelled as such is the pairwise energy between rotamer r=2 of side chain i=2 and rotamer r=2 of side chain j=3. If the template is held fixed, if all possible rotamers for all side chains are accessible from a rotamer library and if a suitable Energy Function is used, the two types of energy terms can be pre-computed for all rotamers (and pairwise combinations) of all flexible side chains of the protein. They can be stored in an appropriate data structure for rapid lookup when needed during execution of the FASTER computations. The Eisenmenger structure corresponds to the assignment, for each flexible side chain i, of the rotamer r having the lowest value for $E(r_i)$. In the picture, a hypothetical example of such structure is given by the black rotamers, assuming that their $E(r_i)$ values are lower than those of the grey rotamers.

In general, the FASTER method uses the input data and a specific method described in detail below, to calculate the energetically best possible 3D-structure (conformation) for all desired side chains on a given main chain. In a preferred embodiment, the algorithm pre-calculates and/or stores a number of data derived from the input data in the form of data structures or sets of data structures, before starting the actual conformation prediction routines. These data preferably include (i) an array containing the atomic co-ordinates of the biomolecule in a starting conformation, i.e. the structure as retrieved from e.g. the PDB of Brooks et al. in *J. Comput. Chem* (1983) 4:187-217, (ii) an internally stored description of the rotamer library, (iii) an internally stored list of flexible residue side chains, as well as a reference or starting conformation where the internal geometry of the side chains (bond lengths and angles) is either imposed by the user, derived from an experimentally determined structure or computer-generated on the basis of standard geometry rules, (iv) separate arrays containing various properties of template atoms and flexible side chains (including, for instance, one- and three-letter codes for the side-chain type, the number of side-chain rotamers, rotameric torsion angles, physico-chemical properties of the atoms in a side chain such as chemical type, $C_\beta$-$C_\beta$ distances; no classification is made regarding the appearance of a side chain in the core, boundary or at the surface of the molecule), (v) an internally stored data set containing the total internal energy of the template, the total internal energies of all flexible side-chain rotamers and their interaction energies with the template, and the side-chain/side-chain interaction energies for all pairs of flexible side chains in all available rotameric conformations. Hereafter, the internal energies of side-chain rotamers, including their interaction with the template, are called rotamer/template interactions and noted $E(r_i)$, where E denotes the sum of the latter two energy components for a flexible side chain i in a rotameric conformation $r_i$. The pairwise interactions between side-chain rotamers are called rotamer/rotamer interactions or pair energies and noted $E(r_i,r_j)$, where E denotes the pairwise interaction between two flexible side chains i and j in rotameric conformations $r_i$ and $r_j$, respectively. FIG. 3 illustrates these energy contributions.

Overview of Faster Routines

In a preferred embodiment (see FIG. 4), FASTER method runs through four different program passes in a sequential way: (1) "Iterative Batch Relaxation" (iBR), (2) "Conditional Iterative Batch Relaxation" (ciBR), (3) "Single residue Perturbation-, Relaxation" (sPR) and (4) "Double residue Perturbation-Relaxation" (dPR). In a less preferred embodiment, some of these passes may be skipped, thus influencing to some extent the overall performance of the algorithm. For instance, the iBR and ciBR passes are intended as preparative routines to enhance the performance of the sPR pass and are not mandatory. Yet they are able to produce already moderately accurate results. The sPR pass is considered as the most important sub-step. Still, in extreme cases where a high computational speed is essential (in such case, either one or both of the iBR and ciBR sub-steps should be used), even the sPR pass can be suppressed, although a substantial loss in accuracy is to be expected. The dPR pass is mainly intended to further improve the quality of the computed structure after application of passes 1 and/or 2 and/or 3, albeit at the cost of a higher computational effort.

Starting Structure

Since the FASTER algorithm includes an iterative optimisation method, a starting structure for the flexible side chains is required. "Starting structure" means the initial assignment of a particular rotamer from the library at each flexible residue position, which defines a unique global structure. In a preferred embodiment, the starting structure is the structure in which each flexible side chain is assigned the rotamer displaying the best possible interaction with the template, ignoring other side chains, which corresponds to the Eisenmenger structure and is further exemplified in FIG. 3. In a less preferred embodiment, a starting structure may be for instance a randomised conformation, in which case the conversion of the iteration steps in the different passes will usually become somewhat less effective. The starting conformation is stored as a set of values, defined for all flexible side chains, and where each value refers to a specific rotamer for the side chain, as known in the rotamer library. Since the template is by definition fixed and the only structural variability resides in the side chains, this set of values unambiguously defines a global conformation where a unique rotamer is assigned to each flexible side chain. Any such global conformation is referred to as an "IMEC". Whereas the notation IMEC corresponds to a global conformation, the notation $IMEC_i$ is used to refer to the value of a specific element of an IMEC, namely the rotameric state of side chain i. Clearly, the data set containing the $IMEC_i$ values (together defining an IMEC) is one of the basic elements of the FASTER algorithm as it defines the global side-chain conformation that is updated regularly during execution of the different iteration steps. At the end of the computations, this data structure represents the final computed structure.

Pass 1, Iterative Batch Relaxation (iBR).

Figure 5:
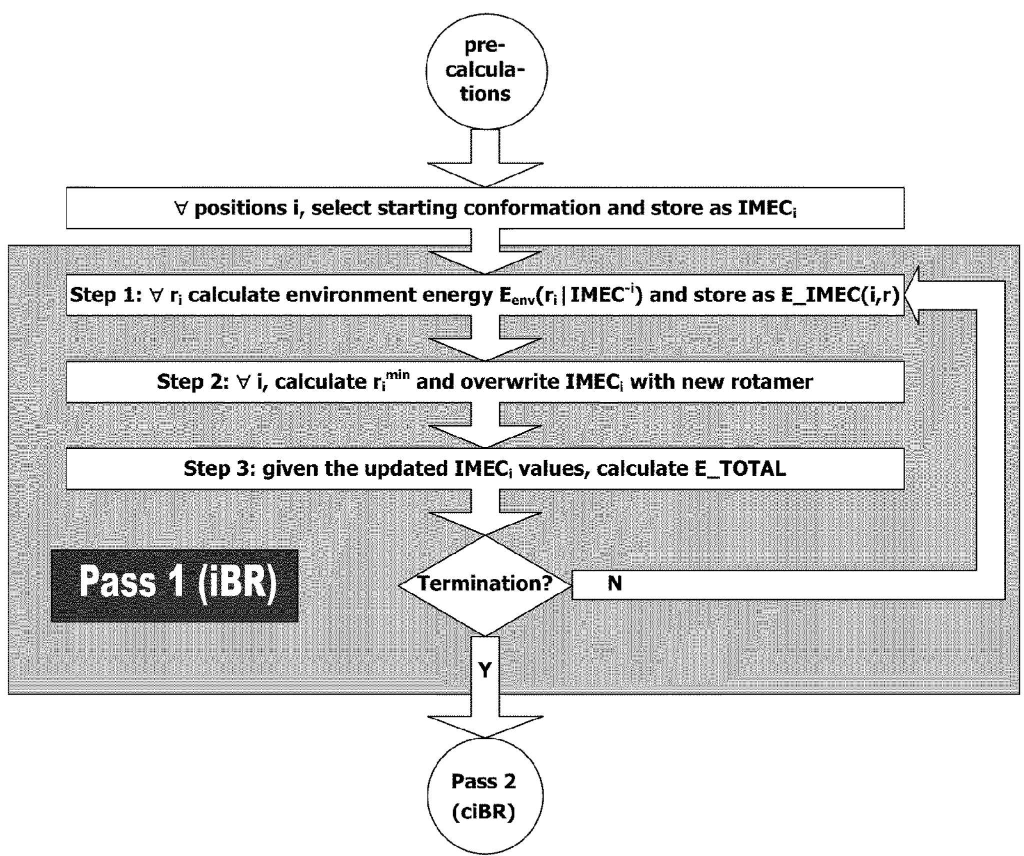
FIG. 5 illustrates method steps and a program flow of pass 1, Iterative Batch Relaxation (iBR), of an embodiment of the method of the invention.

The iBR pass (see FIG. 5) is a preparative, practical and considerably reduced implementation of the basic perturbation/relaxation/evaluation approach. In this step, all perturbation events are disabled and the evaluation steps mainly play an informational role. Thus the iBR pass essentially consists of only relaxation events and is repeated until a termination condition is reached. Each of the iteration cycles in pass 1 consists of three sub-steps. In the first sub-step, for all rotamers of each flexible side chain i, the total energy in the current environment of temporarily assigned side-chain rotamers is calculated. This is called "environment energy" and noted as $E_{env}(r_i|IMEC^{-i})$, to be read as the environment energy of rotamer r of flexible side chain i given the current IMEC for all side chains except i. It can also be understood as the total energy a rotamer feels in a temporarily frozen environmental conformation. $E_{env}(r_i|IMEC^{-i})$ can be mathematically computed as $$E_{env}(r_i \mid IMEC^{-i}) = E(r_i) + \sum_{j=1}^{N} E(r_i, IMEC_j); \quad j \neq i \qquad \text{(eq. 1)}$$

where N is the number of flexible side chains, $E(r_i)$ is the rotamer/template interaction energy and $E(r_i,IMEC_j)$ is the pairwise energy between $r_i$ and the IMEC rotamer of side chain j. In the first step of pass 1 all $E_{env}(r_i|IMEC^{-i})$ values are calculated and stored in a two-dimensional data structure containing the values referred to as E_IMEC(i,r).

In the second sub-step, the algorithm uses a deterministic selection criterion by searching, for each residue i, the rotamer displaying the minimal environment energy, hereafter written as $r_i^{min}$ and defined as $$r_i^{min} = \min_r \text{E\_IMEC}(i, r) \quad \text{(eq. 2)}$$

The value of each selected rotamer $r_i^{min}$ is transferred to the IMEC data set (containing the $IMEC_i$ values) immediately after calculation, where previously stored values are overwritten. Importantly in this second sub-step, the environment energies are not updated each time after a $r_i^{min}$ selection. Updates of the E_IMEC(i,r) data are performed only in a next iteration cycle (in sub-step 1). Such approach is referred to as a "batch mode" (as opposed to "gradual mode"), having the main advantage that all side chains are given an equal chance for relaxation within a constant environment. This makes the conformational search essentially independent of the order in which the side chains are relaxed. Another important advantage is that fewer updates of the E_IMEC(i,r) values are needed, which has a beneficial influence on the computational performance. A possible disadvantage, however, is that side chains changing their rotameric state are "unaware" of other conformational changes during the same iteration cycle, which may locally lead to energetical conflicts between pairs of side chains whereas globally the whole system may be prone to get trapped in an oscillation between two high-energy states (see PASS 2).

Finally, in the third sub-step the total energy, E_TOTAL, is calculated (this sub-step of pass 1 can also be envisaged as the third step of the basic perturbation/relaxation/evaluation cycle). This is conveniently done by using the results of the second sub-step and the following equation:

$$\text{E\_TOTAL} = \text{E\_TEMPLATE} + \sum_{i=1}^{N} E(IMEC_i) + \sum_{i=1}^{N-1} \sum_{j=i+1}^{N} E(IMEC_i, IMEC_j) \quad \text{(eq. 3)}$$

Here, E_TEMPLATE is the pre-computed template self energy, i.e. the sum of all atomic interactions within the template. The values $E(IMEC_i)$ and $E(IMEC_i, IMEC_j)$ are the rotamer/template and the pairwise rotamer/rotamer interaction energies, respectively, where said rotamers are those resulting from the relaxation operations in the second sub-step.

The value computed using equation 3 corresponds to the total energy of the biomolecule and measures the quality of the global structure. It may conveniently be displayed on the computer screen. Importantly, sub-step 3 does not influence the result of sub-step 1 in the next iteration cycle and is therefore optional.

The three sub-steps described above are executed in a cyclic, iterative way until one of the following termination criteria is reached: (1) E_TOTAL after the last iteration cycle has the same value as after the last but one cycle, (2) E_TOTAL after the last cycle has the same value as after the last but two cycles (which normally means that the iteration process has started oscillating), (3) a number of MAX_CYCLES_P1 iteration cycles have been performed, where MAX_CYCLES_P1 is a user-defined parameter with a value usually ranging between 5 and 20. If the optional step 3 is not executed, then only the third termination criterion can be used.

As explained before, the notion of "batch relaxation" refers to the fact that, in the preferred embodiment, step 2 is performed for the whole "batch" of all flexible side chains and that step 3 (or step 1 if step 3 is skipped) is executed only after step 2 is completed. However, in a less preferred embodiment called gradual relaxation, it is possible to execute step 3 (or step 1 if step 3 is skipped) immediately after having processed in step 2 any number of side chains less than the whole batch, typically one side chain at a time. This is less preferred in view of the intrinsic slower speed and the dependence on the order in which the side chains are considered for relaxation.

Alternative embodiments of iBR are possible. For instance, sub-steps 1 and 2 may be integrated into a single sub-step, where the $E_{env}(r_i \mid IMEC^{-i})$ and $r_i^{min}$ calculations are performed immediately in succession for each flexible side chain. Such integration does not influence the final results and negligibly influences the computational speed. It is therefore considered as an equally preferred embodiment of the iBR approach.

In another embodiment, sub-steps 1-3 are performed in a cyclic way enabling, in principle, a number of permutations. For instance, sub-steps 2, 3 and 1 can be permuted to sub-steps 1, 2 and 3, respectively. If an iteration cycle starts with sub-step 2 as the first sub-step, then the initialisation operations must be complemented with an additional step comprising the calculation and storage of environment energies. Also, sub-step 3 can be made first, provided that initialisations are suitably adapted. Though equally effective, such permutations are somewhat less preferred.

A more important variation is the introduction of one or more filtering steps in between sub-steps 2 and 3 of the iBR routine. More specifically, it is possible to modify the selection of side chains to be relaxed, as well as the selection of rotamers during the relaxation steps. For instance, rather than considering all flexible side chains in one iteration cycle, it can be desirable to relax only a sub-set of them. Also, instead of selecting rotamers having a minimal environment energy within the context of the current IMEC, sub-optimal rotamers can be selected. Such variations may be helpful to avoid the system being trapped in a local minimum. Also, applying different filtering steps will generally lead to different results which can be post-evaluated according to the requirements of the user. The specific selection of side-chains to be relaxed and the rotamers to be taken into account for this purpose can be performed in a variety of ways. Most often, this selection can be based on energetic properties of the rotamers (e.g. absolute or relative rotamer/template, pair and/or environment energies), specific properties of individual side chains (e.g. a differential treatment based on side-chain type), features of the template (e.g. the local secondary structure), stochastic elements (e.g. selecting side-chains according to some probability distribution), or any combination thereof. Importantly, all aforementioned filtering possibilities should be considered as additional steps, not forming part of the preferred embodiment of the iBR pass.

Pass 2, Conditional Iterative Batch Relaxation (ciBR)

Pass 2 (ciBR) is basically identical to pass 1, except for some major and minor modifications. It continues from the final data provided by the iBR pass, i.e. the data sets containing the $IMEC_i$ and E_IMEC(i,r) values. It consists of the same three basic sub-steps and alternates between sub-step 1 (updating of the E_IMEC(i,r) energies) and sub-step 2 (selection of $r_i^{min}$ rotamers and storing their values in the IMEC data set), but sub-step 3 (calculation of E_TOTAL) is preferably skipped to enhance the computational speed. A more important difference, however, is that the $r_i^{min}$ rotamers as selected in sub-step 2 are accepted only on the basis of a probability coefficient ACC_PROB preferably equal to 0.8. Thus, in statistically 80% of the cases on a purely random basis, a selected $r_i^{min}$ rotamer is accepted and only then, the IMEC data set is overwritten, at the $i^{th}$ element, with that rotamer. Else, the previous rotamer is maintained by leaving the $i^{th}$ element unmodified.

In the process of selection and decision, no attention is paid as to whether newly selected $r_i^{min}$ rotamers are different from those in a previous iteration cycle. Similarly, it makes no difference whether newly selected $r_i^{min}$ rotamers correspond with energetic uphill or downhill movements. Using an acceptance probability coefficient just serves as a simple solution to break the commonly observed oscillation of E_TOTAL in the last iteration cycles of the iBR pass. Clearly, it is not intended to escape from local minima since if the system was in such a minimum after pass 1, then pass 2 would become ineffective as well.

The value ACC_PROB=0.8 results from fine-tuning experiments which showed that this value provides a near-optimal compromise between computational speed and energetic relaxation for 50 test proteins. In a less preferred embodiment ACC_PROB may have any value between about 0.5 and 0.95 or even any value between 0 and 1. The probability coefficient ACC_PROB may also not be kept constant but may be a function of the residue position and/or type, the number of rotamers, pair-energies, environment energies, the iteration cycle, etc. Yet a constant value for ACC_PROB is a suitable choice in order to solve oscillation phenomena.

Since the calculation of E_TOTAL (sub-step 3) is usually skipped in the ciBR pass, the termination condition preferably relies on the number of iteration cycles. In a preferred embodiment, when ACC_PROB equals 0.8, the termination parameter MAX_CYCLES_P2 is set at 20. In less preferred embodiments MAX_CYCLES_P2 should be increased when ACC_PROB is lowered and vice versa. Another important consequence of introducing a stochastic factor is that the final result of this pass is non-deterministic. Although introducing some uncertainty, this property can be usefully exploited by repeating the entire ciBR pass N_REPEATS_P2 times and retaining only the energetically best result as the input data for pass 3. In a preferred embodiment the parameter N_REPEATS_P2 equals 10 although many other embodiments are possible using various combinations of the parameters ACC_PROB, MAX_CYCLES_P2 and N_REPEATS_P2.

Methodologically, the systematic computation of $r_i^{min}$ rotamers for all flexible side chains and the later rejection of a fraction thereof appears to be sub-optimal. It could be argued that the computational efforts spent for the rejected fraction of side chains are useless, as the fraction of side chains to be relaxed can be determined on beforehand and the computations can be restricted to only the side chains belonging to this sub-set. However, this embodiment has the advantages (i) it is the simplest possible embodiment and (ii) the systematic computation of all $r_i^{min}$ rotamers, even for the rejected fraction, leaves the possibility for future optimisations in which the acceptance of rotamers is based on other than stochastic criteria.

Finally pass 1 and/or pass 2 may be performed while unifying side chains to what is generally known in the art as "super-residues" consisting of multiple side chains (for instance pairs) which are treated as singles according to the rules defined by Desmet et al. in *Proceedings of the Pacific Symposium on Biocomputing* (1997), pp. 122-133.

Pass 3, Single-Residue Perturbation/Relaxation (sPR)

The relaxation procedures in passes 1 and 2 may become trapped in some local minimum which is usually different from the GMEC. The sPR pass aims at overcoming this problem, in order to enable further global optimisation, on the basis of the full perturbation/relaxation/evaluation principle. Central to this routine is the systematic, temporary fixation of side chains in a particular conformation (called perturbation) followed by global energetic relaxation, in rotameric space, of all other side chains. Thus, pass 3 is similar to pass 1, enwrapped by a loop over all rotamers which are temporarily fixed. Such a temporary fixation can also be considered as a virtual transfer of the involved side chain to the template. Side chains that are temporarily fixed, merely for the purposes of further energetic relaxation, are not to be confused with the permanently fixed side chains (if any) which are not included in the user-defined list of rotatable side chains.

Figure 6:
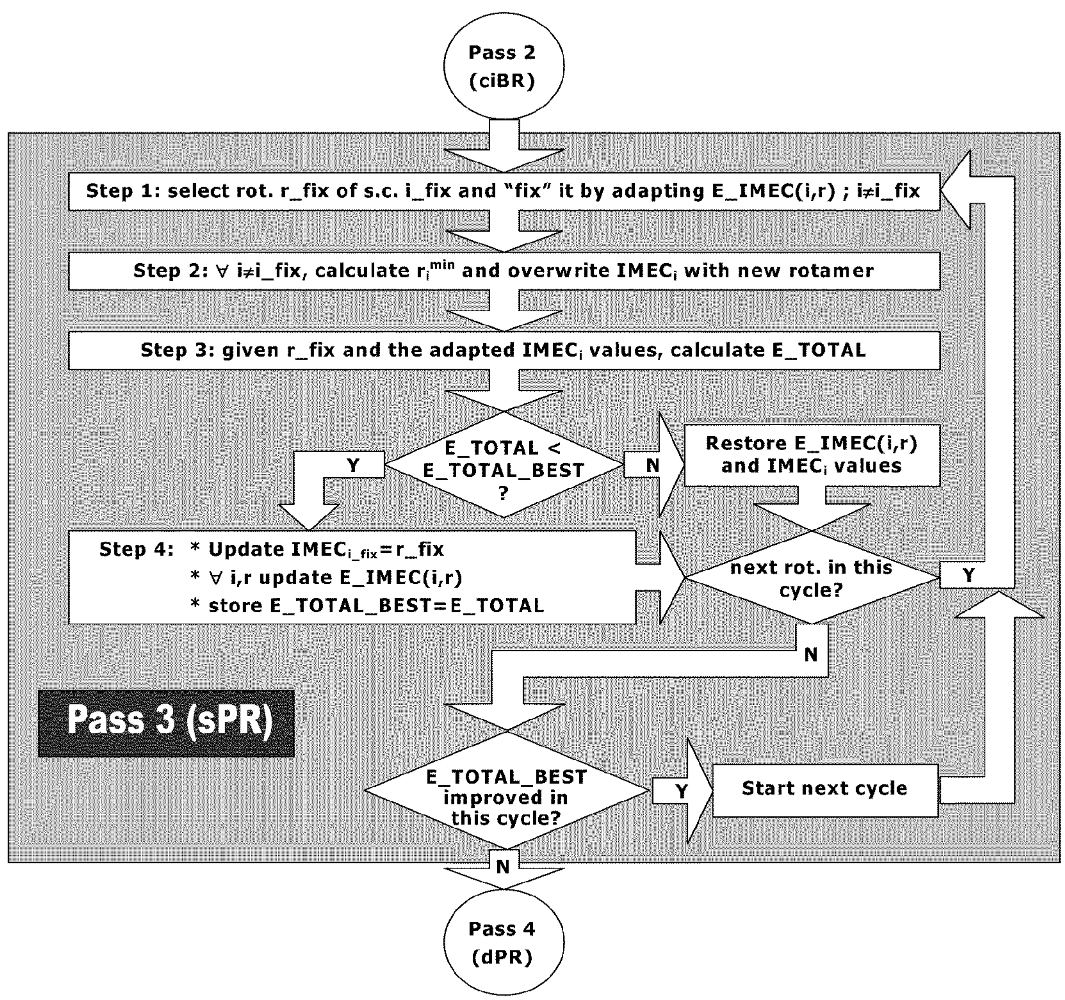
FIG. 6 illustrates method steps and a program flow of pass 3, Single residue. Perturbation/Relaxation (sPR), of an embodiment of the present invention, wherein rot.=rotamer; r_fix=rotamer selected as the rotamer to be temporarily fixed; i_fix=perturbed side chain, i.e. the side chain selected to be temporarily fixed in the rotameric state r_fix; s.c.=side chain.

Concretely (see FIG. 6) in pass 3, each available rotamer (hereafter called the fixed rotamer) of each rotatable side chain (hereafter called perturbed side chain) is temporarily selected and, for each such event, the following actions take place.

In step 1, the actual perturbation step, the rotamer which has been selected to perform perturbation (r_fix), belonging to the perturbed side chain (i_fix), is temporarily fixed. This fixation only needs to occur in a virtual way as it is the effect of the perturbation on the other side chains i ($i \neq i\_fix$), rather than the perturbation itself, that influences the later relaxation step. The primary effect of a perturbation can be easily taken care of by correcting the environment energies of all non-perturbed side chains for the fixed rotamer considered. This is simply accomplished by diminishing all E_IMEC(i,r) values (for $i \neq i\_fix$) with the rotamer/rotamer pair energy before perturbation, $E(r_i, IMEC_{i\_fix})$, and augmenting it with the pair energy after perturbation, $E(r_i, r\_fix_{i\_fix})$. The net effect of this operation is that the environmental side-chain rotamers "feel" the IMEC which has changed at one particular position.

In step 2, the relaxation step, the minimum energy rotamer $r_i^{min}$ according to equation 2 is calculated for all side chains, except the perturbed one, using the adapted E_IMEC(i,r) values. The resulting $r_i^{min}$ rotamers are selected and stored in the data set holding the $IMEC_i$ values. This step is thus identical to sub-step 2 in pass 1, except for the perturbed side chain. Experimental tests have shown that the probability coefficient ACC_PROB is preferably set at 1, which is equivalent to the unconditional acceptance of $r_i^{min}$ rotamers. Also, the number of relaxation cycles after each perturbation is preferably only 1, which means that all side chains are given only one opportunity to adapt to the perturbation. It is assumed that these simple settings are justified because (i) after execution of passes 1 and 2, the system has already reached a relatively low energy state and (ii) the perturbations are systematic and exhaustive, i.e. if a relaxation operation fails due to the simple parameter settings, this may be adjusted in one of the numerous other perturbation/relaxation steps.

Step 3 forms the first part of the evaluation step. Using equation 3, the total energy E_TOTAL is calculated for the system consisting of the perturbed side chain i_fix in rotameric state r_fix and the other side chains i ($i \neq i\_fix$) in their rotameric states as stored in the $IMEC_i$ data structure. Thus, this step is also identical to sub-step 3 of pass 1, except for the perturbed side chain where the fixed rotamer must be used.

Importantly, in step 4 of the sPR pass, a decision is made about whether to accept or reject the full global structure resulting from the perturbation/relaxation operations of steps 1 to 3. For this purpose, the value of E_TOTAL is compared with the value of the system before the current perturbation and only when E_TOTAL is lower than the lowest value previously found, the new IMEC structure is accepted as a whole. In such case, the new global IMEC is consolidated as follows: (1) first, the fixed rotamer, r_fix, is stored in the IMEC data set (note that the latter is not necessary for the environmental side chains as their $r_i^{min}$ rotamers had already been stored automatically during the relaxation step 2), then (2) The values for E_IMEC(i,r) are updated on the basis of equation 1 using the new $IMEC_i$ values (which is similar to sub-step 1 in pass 1), and then (3) the computed value of E_TOTAL, corresponding to the current perturbed/relaxed system, is stored for comparison after the next cycle. Else, i.e. in case E_TOTAL is not better than the lowest value previously found, the program must reset the E_IMEC(i,r) values to those before the perturbation step. Preferably, this is done from a copy of the data set E_IMEC that was taken before executing the perturbation. Also, in a preferred embodiment, the $IMEC_i$ values are restored although this is not absolutely required as they are derived in step 2 from the E_IMEC(i,r) values.

At this point, irrespective of the outcome of the test on E_TOTAL, the algorithm is ready to continue with the next perturbation (if any) or to exit pass 3. In a preferred embodiment, the algorithm infinitely loops back until in a full round of perturbations (for all rotamers of all side chains) no improvement in E_TOTAL has been observed, in which case pass 3 exits. This guarantees that the global conformation has reached a local minimum of second or higher order since all side chains have had the chance to adapt to each single perturbation and no improvement has been detected.

In a preferred embodiment, the flexible side chains are perturbed in a random order. For this purpose, a randomly shuffled list of flexible side chains is constructed prior to starting the sPR pass. In a less preferred embodiment, the flexible side chains are perturbed in the same order as they appear in the sequence. Alternatively, the order of perturbations may be based on energetic or topological properties of the rotamers or on the type of the side chains.

Pass 4, Double-Residue Perturbation/Relaxation (dPR)

In pass 4, exactly the same strategy is followed as in pass 3, except that two side chains are perturbed simultaneously by systematically fixing all combinations of rotamer pairs. However, the efficiency of finding energetically better conformations, i.e. lower values for E_TOTAL, is strongly dependent on the distance between the perturbed residues. Therefore, in a preferred embodiment, only couples of side chains (i,j) are selected that are proximate in 3D-space. A convenient selection criterion for this purpose is when the distance between their $C_\beta$-atoms is e.g. below $(6.0+n_i+n_j)$ Å, where $n_i$ and $n_j$ are a measure of the size of side chains i and j respectively. More precisely, n may be the number of heavy atoms counted from the $C_\beta$-atom (included) along the longest branch in the side chain. In another equally preferred embodiment, the selection of couples of side chains to be perturbed occurs by choosing those having a non-zero pair interaction for at least one of their combinations of rotamers.

The dPR pass, being the slowest routine, is optional. It is intended to systematically remove local minima of the second order so that, at the end, the global conformation resides in a local minimum of the third or higher order. However, the latter is only guaranteed provided that (1) all possible pairs of side chains have been perturbed in all possible combinations of rotamers and (2) in one full dPR pass not any global conformation with lower E_TOTAL has appeared (which requires iterative application of the whole dPR pass), two conditions which are not preferred for reasons of computational speed. In practice, the preferred embodiment is a dPR pass which (i) limits the selection of perturbed side chains by one of the two methods described above and (ii) performs only one iterative round of perturbations.

The dPR pass can be easily extended towards simultaneous perturbation/relaxation of multiple side chains, which is referred to as "Multiple residue perturbation/relaxation" (mPR), similarly to the extension from the sPR to the dPR routine. From a perspective of computational performance however, this extension may be problematic as the number of possible combinations increases dramatically for multiple perturbations. Yet, if some criteria can be defined that allow a substantial reduction of the number of perturbations performed while not affecting the relaxation events, such mPR routine may become practically useful, as hereinafter described.

Further Methodological and Algorithmical Optimisations

The computational speed of the FASTER method strongly depends on the total number of side-chain rotamers to be fixed in the sPR and dPR passes. In order to further increase computational speed, optimisation procedures can be introduced that aim at reducing the number of rotamers to be considered while not affecting the final predicted side-chain conformations.

A most important optimisation is a combination of part of the DEE algorithm with the FASTER algorithm, with the effect of pre-eliminating rotamers before the start of the FASTER routines. For instance, as in the original DEE algorithm, rotamers for which the interaction energy with the template $E(r_i)$ is higher than MAX_E_ABSOLUTE kcal $mol^{-1}$ or higher than MAX_E_RELATIVE kcal $mol^{-1}$ above the lowest value for the same side chain, may be discarded from further consideration. In a preferred embodiment, MAX_E_ABSOLUTE and MAX_E_RELATIVE are in the range of about 20 to 40 kcal $mol^{-1}$ and 10 to 20 kcal $mol^{-1}$ respectively, whereas in a less preferred embodiment these parameters can be set to any other positive value. In another preferred embodiment, the unmodified original DEE routine for single side chains described by Desmet et al. in *Nature* (1992) 356:539-542 may be applied and may be followed by the DEE routine for single residues Lasters et al. in *J. Protein Eng.* (1995) 8:815-822, both being performed in an iterative way until in a given iteration cycle less than e.g. 5% of the total number of remaining rotamers have been eliminated. Other DEE routines, including but not limited to those for side chain pairs, may also be used, although they may consume an amount of CPU-time that is comparable or greater than the FASTER routines themselves, which makes such embodiments less preferred.

A second program optimisation concerning the dPR pass, and exploiting the experimental finding that the global side-chain conformation obtained after the sPR pass already closely approximates the GMEC, postulates a practically useful criterion that predicts whether a particular rotamer does not belong to the GMEC. Concretely, rotamers $r_i$ for which the rotamer/template interaction energy, augmented with the minimal pair interaction with each environmental side chain, is larger than the total environment energy of the IMEC rotamer of the same side chain, are assumed to be incompatible with the GMEC, as expressed by equation 4:

$$E(r_i) + \sum_{j=1}^{N} \min_{r_j} E(r_i, r_j) > E_{env}(IMEC_i \mid IMEC^{-i}); \quad (j \neq i) \qquad \text{(eq. 4)}$$

where the definitions of all variables and functions are the same as in equation 1 (note that $IMEC_i$ refers to a single rotamer, i.e. the IMEC rotamer for side chain i, whereas $IMEC^{-i}$ refers to the global IMEC structure where side chain i is ignored). The min-function at the left-hand side of expression 4 generates the minimal environmental pair interactions with rotamer $r_i$. When substituting equation 1 into equation 4, a more explicit criterion according to equation 5 is obtained.

$$E(r_i) + \sum_{\substack{j=1 \\ (j \neq i)}}^{N} \min_{r_j} E(r_i, r_j) > E(IMEC_i) + \sum_{j=1}^{N} E(IMEC_i, IMEC_j); \quad \text{(eq. 5)}$$

Importantly, rotamers $r_i$ that match this criterion are not eliminated, but just ignored when selecting rotamer pairs for perturbation in step 1 of the dPR pass, i.e. they remain present during the relaxation step 2. In a preferred embodiment, prior to the start of pass 4, all rotamers are screened using equation 5 and rotamers matching this criterion are flagged in a specific array. Screening is done iteratively in maximally MAX_CYCLES_P4_PRE cycles. Flagged rotamers may also be ignored in consecutive cycles when evaluating the min-function at the left hand side of equation 5. Preferably, MAX_CYCLES_P4_PRE equals 1 or 2, or 3 to 4 in less preferred embodiments. Higher values for MAX_CYCLES_P4_PRE result in a too limited number of non-flagged rotamers that will be perturbed in the dPR pass, so that the perturbation/relaxation steps become less effective. When this parameter is set to the preferred value of 2, the computational speed of the dPR pass is significantly decreased while there is no appreciable influence on the relaxation events and thus on the quality of the final structure.

USE of sPR Data to Predict Conformational Flexibility

The sPR pass provides an embodiment of the present invention in which the conformational flexibility of individual side chains at specific positions on a 3-D biomolecule backbone structure are predicted without significantly increasing the computational load as it can be performed on basis of data that is computed anyway.

Concretely, during normal execution of the sPR pass, the values for E_TOTAL (computed in step 3) after perturbation (step 1) and relaxation (step 2) can be stored for each fixed rotamer r_fix of side chain i_fix in a data set holding the E_PR(i,r) values, i.e. the total energy (E) of the system after perturbation (P) of side chain i in rotameric state r and relaxation (R) of the other side chains, or (briefly) the perturbation/relaxation energy of rotamer $r_i$. During the various iteration cycles of the sPR pass, these values may be overwritten so that the E_PR(i,r) data set contains the most recent values at any time, including when the program exits pass 3.

An interesting property of the sPR pass is that an exit condition is met only when a full iteration cycle (perturbation of all i,r) has been performed without obtaining a better E_TOTAL value so that E_TOTAL_BEST represents the energy of the global conformation that is guaranteed to be in a local minimum of second or higher order. A statistically significant number of test experiments on different non-homologous proteins has shown that the total energy of this local minimum is generally extremely close to that of the GMEC (to within about 0.008 kcal $mol^{-1}$ per residue on average). This means that, after the last cycle, the E_PR(i,r) values represent the total energies of the global structures which have been perturbed (and relaxed) from a near-GMEC conformation. Consequently, the difference between a E_PR(i,r) value and E_TOTAL_BEST, stored as DELTA_E_PR(i, r), is a very accurate measure of the true perturbation energy to modify a specific rotamer of the GMEC, noted as $\Delta E(r_i)$.

In a preferred embodiment, right before exiting the sPR routine, these perturbation energies are calculated using equation 6 and stored for later analysis.

$$\Delta E(r_i) \approx \text{DELTA\_E\_PR}(i,r) = E\_PR(i,r) - E\_\text{TOTAL\_BEST} \quad \text{(eq. 6)}$$

Such a data analysis, although not essential for the FASTER method, provides a classification of side chains as "rigid" or "flexible" on the basis of the number of rotamers having a perturbation energy below a given cut-off value, compared with the original number of rotamers in the rotamer library.

Importantly, if a full set of perturbation values is desired, care must be taken in eliminating rotamers prior to the FASTER routines (see section on algorithmical optimisations): since DEE pre-elimination routines are very effective, rotamers might be eliminated that have a low "acceptable" perturbation energy. Therefore, such routines are preferably disabled when performing a flexibility analysis. In contrast, the pre-elimination of rotamers on the basis of absolute and relative threshold energies (using e.g. the parameters MAX_EAB SOLUTE or MAX_E_RELATIVE) cannot influence the flexibility results if the preferred threshold parameter values are chosen.

Use of the Faster Method for Protein Design

Although the FASTER method has been conceived to search the conformational space of a set of side chains attached to a given biomolecule main chain, a further embodiment of the present invention provides exploration of the reachable sequence space of a protein. More specifically, by a small modification of the sPR pass, it is possible to estimate the energetic cost required to substitute, at specific positions, single amino acid side chains into all other natural residue types. The sPR pass in the FASTER algorithm basically evaluates, for all rotamers of all rotatable side chains, the likelihood of a particular rotamer at that position. In addition, this pass assesses how the environmental side chains can adapt to a perturbed residue, the side chain of which is put in some fixed conformational state. The value for $\Delta E(r_i)$ as defined in equation 6 thus represents the energetic cost to rotate a side chain i from the GMEC structure into rotamer r. Similarly altering side chains by mutating them into different side-chain types in stead of conformations, followed by optimising the conformation of its environment and calculating the global change in potential energy ($\Delta E_{mutation}$), is also applicable. This in fact means extending the definition of a rotamer from a sterically acceptable side-chain 3D-structure of a single amino acid to a sterically acceptable 3D-structure of one of a collection of amino acids.

This approach was originally referred to as "inverse folding" since it searches for the optimal sequence given a 3D-structure, in contrast to "protein folding" which searches for the optimal 3D-structure given a particular sequence. It has found now valuable applications in the form of "protein design" which aims at optimising the sequence of a protein with respect to stability or affinity. Until now, its most advanced implementation was based on DEE computations which are very slow for this type of application and does not offer an optimal solution as it must be combined with a stochastical or statistical method.

The present invention provides an improved method for "inverse folding" based on the perturbation/relaxation concept, which optimally exploits its features, i.e. computational speed and prediction accuracy. For this purpose, the above-described FASTER algorithm can be kept while adding to the sPR pass an extra loop over all possible residue types, in between the loop that runs over all side chains and the loop over all conformations. This method is given hereafter in a prototypical language:

```
∀ positions i; i=1→N_positions
  ∀ side-chain types j; j=1→N_types          ⇐ EXTRA LOOP
    ∀ conformations k; k=1→N_rotamers
      Step 1: At position i, perturb (i.e. fix) side-chain type j in
      conformation k
      Step 2: Relax neighbouring residues to this perturbation
      Step 3: Calculate E_TOTAL(i,j,k)
    Next k
    Calculate minimal value for E_TOTAL(i,j,k) over all k
    Store said minimal value as E_TOTAL_MIN(i,j)
    Calculate ΔE_mutation(i,j) = E_TOTAL_MIN(i,j) −
    E_TOTAL_MIN(i,WT)
  Next j
Next i
```

wherein $N_{positions}$ is the number of residue positions that are considered in the experiment, $N_{types}$ is the number of amino acid side-chain types that are allowed at each position and $N_{rotamers}$ is the number of rotamers that are known in the rotamer library for residue type j. WT is the abbreviation for "wild type", i.e. the original amino acid sequence of a protein before mutation, i.e. in this context the specific amino acid type in the original sequence at the position i before perturbation.

Steps 1 to 3 are equivalent to the same steps in the sPR pass of the FASTER method. The net result after executing step 3 is that the total energy is known for the original structure in which a particular side chain (j) in a particular rotameric conformation (k) is introduced at a particular residue position (i) and to which the environmental side chains have adapted their conformation by the same relaxation process as in the FASTER sPR pass. After looping over all conformations k, the program searches for the minimal value of E_TOTAL(i,j,k), stored as E_TOTAL_MIN(i,j) and corresponding with the computed potential energy of a structure in which a point mutation j has occurred at position i. After computing E_TOTAL_MIN(i,WT) by the standard FASTER method, then this value can be subtracted from all values for E_TOTAL_MIN (i,j), which leads to a net estimate for the energetic cost to mutate the WT structure by a point mutation j at position i. In other words, $\Delta E_{mutation}(i,j)$ may be interpreted as a fair estimate of the true substitution energy. Similarly, this method can be extended to the dPR pass in order to estimate the substitution energy for double mutants and can be further extended towards triple and higher order mutations albeit at the cost of severely increased computation times if the method is systematically applied to all possible combinations of mutations.

Execution Environment

The present invention may be implemented on a computing device, e.g. a personal computer or a work station, which has an input device for inputting a complete or partial description of the molecular structure of a biomolecule. The said computing device should be adapted to run software carrying out any of the methods in accordance with the present invention. The computer device may be a server connected to a data communications transmission means such as the Internet. A script file including the details of the experimental set-up may be sent from a near location, e.g. a terminal, to a remote, i.e. second location, at which the server resides. The processing engine of the computing device receives this data and outputs back to a near location, along the same or a different communication line, useful information related to the said molecular structure, e.g. a 3D-representation or the lowest global energy of the biomolecule, the results of a flexibility analysis (including flexibility coefficients) or any other information observed during the modelling process.

Figure 13:
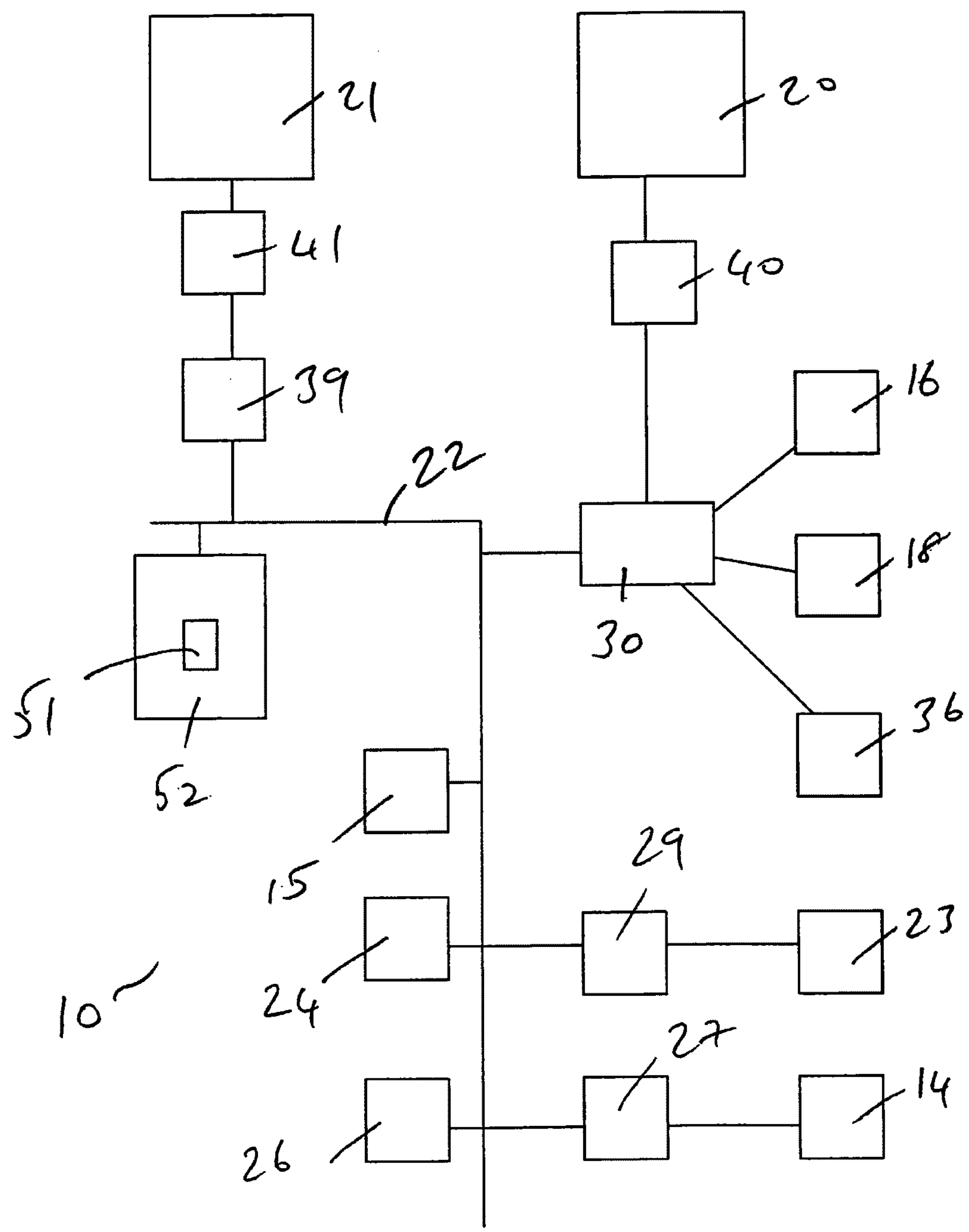
FIG. 13 is a schematic representation of a computer with which may be used for carrying out any of the methods in accordance with the present invention. Numbers are used in the schematic representation to indicate each component. The Computer 10 shown in the figure includes a Central Processing Unit ("CPU") 15, such as a conventional microprocessor of which a Pentium III processor supplied by Intel Corp. USA is only an example, and a number of other units interconnected via system bus 22. The computer 10 includes at least one memory. Memory may include any of a variety of data storage devices known to the skilled person such as random-access memory ("RAM"), read-only memory ("ROM"), and non-volatile read/write memory such as a hard disc as known to the skilled person. For example, computer 10 may further include random-access memory ("RAM") 24, read-only memory ("ROM") 26, as well as an optional display adapter 27 for connecting system bus 22 to an optional video display terminal 14, and an optional input/output (I/O) adapter 29 for connecting peripheral devices (e. g., disk and tape drives 23) to system bus 22. Video display terminal 14 can be the visual output of computer 10, which can be any suitable display device such as a CRT-based video display well-known in the art of computer hardware. However, with a portable or notebook-based computer, video display terminal 14 can be replaced with a LCD-based or a gas plasma-based flat-panel display. Computer 10 further includes user interface adapter 30 for connecting a keyboard 16, mouse 18, optional speaker 36, as well as allowing optional physical value inputs from physical value capture devices 40 of an external system 20. The devices 40 may be any suitable equipment for capturing physical parameters required in the execution of the present invention. Additional or alternative devices 41 for capturing physical parameters of an additional or alternative external system 21 may also connected to bus 22 via a communication adapter 39 connecting computer 10 to a data network such as the Internet, an Intranet a Local or Wide Area network (LAN or WAN) or a CAN.

FIG. 13 is a schematic representation of a computing system which can be utilized in accordance with the method and system of the present invention. The system and method provided by the present invention can be implemented with the computing system depicted in FIG. 13. A computer 10 is depicted which may include a video display terminal 14, a data input means such as a keyboard 16, and a graphic user interface indicating means such as a mouse 18. Computer 10 may be implemented as a general purpose computer.

Computer 10 includes a Central Processing Unit ("CPU") 15, such as a conventional microprocessor of which a Pentium III processor supplied by Intel Corp. USA is only an example, and a number of other units interconnected via system bus 22. The computer 10 includes at least one memory. Memory may include any of a variety of data storage devices known to the skilled person such as random-access memory ("RAM"), read-only memory ("ROM"), non-volatile read/write memory such as a hard disc as known to the skilled person. For example, computer 10 may further include random-access memory ("RAM") 24, read-only memory ("ROM") 26, as well as an optional display adapter 27 for connecting system bus 22 to an optional video display terminal 14, and an optional input/output (I/O) adapter 29 for connecting peripheral devices (e.g., disk and tape drives 23) to system bus 22. Video display terminal 14 can be the visual output of computer 10, which can be any suitable display device such as a CRT-based video display well-known in the art of computer hardware. However, with a portable or notebook-based computer, video display terminal 14 can be replaced with a LCD-based or a gas plasma-based flat-panel display. Computer 10 further includes user interface adapter 30 for connecting a keyboard 16, mouse 18, optional speaker 36, as well as allowing optional physical value inputs from physical value capture devices 40 of an external system 20. The devices 40 may be any suitable equipment for capturing physical parameters required in the execution of the present invention. Additional or alternative devices 41 for capturing physical parameters of an additional or alternative external system 21 may also connected to bus 22 via a communication adapter 39 connecting computer 10 to a data network such as the Internet, an Intranet a Local or Wide Area network (LAN or WAN) or a CAN. The term "physical value capture device" includes devices which provide values of parameters of a system, e.g. they may be an information network or databases such as a rotamer library.

Computer 10 also includes a graphical user interface that resides within a machine-readable media to direct the operation of computer 10. Any suitable machine-readable media may retain the graphical user interface, such as a random access memory (RAM) 24, a read-only memory (ROM) 26, a magnetic diskette, magnetic tape, or optical disk (the last three being located in disk and tape drives 23). Any suitable operating system and associated graphical user interface (e.g., Microsoft Windows) may direct CPU 15. In addition, computer 10 includes a control program 51 which resides within computer memory storage 52. Control program 51 contains instructions that when executed on CPU 15 carries out the operations described with respect to the methods of the present invention as described above.

Those skilled in the art will appreciate that the hardware represented in FIG. 13 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already described.

In the example depicted in FIG. 13, the computer program product (i.e. control program 51 for executing methods in accordance with the present invention comprising instruction means in accordance with the present invention) can reside in computer storage 52. However, it is important that while the present invention has been, and will continue to be, that those skilled in the art will appreciate that the methods of the present invention are capable of being distributed as a program product in a variety of forms, and that the present invention applies equally regardless of the particular type of signal bearing media used to actually carry out the distribution. Examples of computer readable signal bearing media include: recordable type media such as floppy disks and CD ROMs and transmission type media such as digital and analogue communication links.

Further Embodiments

Referring to the second embodiment as disclosed in the SUMMARY OF THE INVENTION, and referring to the foregoing detailed description, the following constitute specific and optional modes of implementation of the invention:

the information outputted in step (j) is a global or partial representation of the 3D-structure of said biomolecule, or the global cost calculated in step (g), or a data structure comprising a set of data extracted from the calculations in step (f).

the number of residue portions in the first set present in step (a) is at least 5.

a conformational space, calculated as the product of the number of rotamers provided in step (c) for each residue portion of the first set, is at least 1,000,000,000, or a larger conformational space is subdivided into smaller fractions and distributed over separate executions of the method.

at least 30% of the rotamers provided in step (c) for each residue portion of the first set are selected at least once for temporary fixation in step (e), or in step (c) a redundant rotamer library is used, so as to stay below the threshold of 30%.

at least 100 perturbation steps in accordance with step (e) are performed, or any larger number of perturbation steps is distributed over separate executions of the method wherein less than 100 perturbation steps are performed.

in step (e) the third set of residue portions comprises at least 30% of the residue portions of the first set forming the immediate environment of the one or more perturbed residue portions of the second set, wherein the residue portions forming the immediate environment of the perturbed residue portions are those residue portions having at least one atom closer than 0.4 nanometer to any atom of a perturbed residue portion in the current global structure defined in step (d) or step (h), or wherein the same perturbations, in combination with different third sets of residue portions are distributed over different optimization cycles so as to stay below the threshold of 30%.

the number of said rotamers considered in the relaxation step (f), averaged over all the residue portions of the third set provided in step (e), amounts to at least 20% of the average number of rotamers provided in step (c) or the number of rotamers provided in step (c) is made redundant so as to stay below the threshold of 20%.

the residue portions of the first set formed in step (a) comprise at least those atoms which undergo spatial displacement when applying the different rotamers provided in step (c), the remainder of the atoms of said biomolecule being included in the template.

the energetic cost function of step (b) is any function which allows to calculate a quantitative measure of the free or potential energy of any global structure of said biomolecule and any set of residue portions thereof.

the rotamers provided in step (c) are descriptions of potential three-dimensional structures of the residue portions of the first set, where, for each residue portion of the first set, the three-dimensional structures represent different conformations of one or more single residue types.

the rotamers provided in step (c) are determined by a statistical analysis of experimentally determined biomolecular structures, or by application of physico-chemical principles.

the rotamers provided in step (c) result from a computational generation of different three-dimensional structures of single residue types within the context of a molecular reference structure, and optionally further result from the energetic analysis, using a cost function as defined in step (b), of the computationally generated three-dimensional structures.

the rotamers provided in step (c) are side-chain rotamers, or are combined main-chain/side-chain rotamers.

some of the rotamers provided in step (c) are eliminated on the basis of their energetic interaction, calculated using a cost function as defined in step (b), with the template defined in step (a), or by applying dead-end elimination.

the assignment of rotamers in step (d) is performed while using the rotamers provided in step (c) in combination with either a random selection method or with an energetic analysis, using a cost function as defined in step (b), of the rotamers provided within the context of the template as defined in step (a).

the method comprises an additional step in which the energetic interactions between the rotamers provided in step (c) and the template defined in step (a) and/or between pairs of rotamers belonging to different residue portions of the first set are calculated, using an energetic cost function as defined in step (b), stored in a data structure and used in the optimization cycle.

the second set of perturbed residue portions provided in step (e) is selected from the first set of residue portions in a random way, or in accordance with the residue sequence of the biomolecule.

in step (e) of each optimization cycle, the second set of perturbed residue portions consists of a single residue portion, or two residue portions, or three or more residue portions.

in step (e), the temporarily fixed rotameric state of each perturbed residue portion is selected from the set of step (c) in a random way, or while excluding any random selection method.

in step (e), the temporarily fixed rotameric state of each perturbed residue portion is selected from the set of step (c) while excluding any rotamer R for a perturbed residue portion P, for which a first energetic term A is higher than a second energetic term B, the term A being calculated as the interaction energy of the rotamer R with the template augmented with the sum of the best possible pairwise interaction energies with R, given the rotamers provided in step (c), and the term B being calculated as the interaction energy of any rotamer S for the residue portion P with the template, augmented with the pairwise interaction energies with the rotamers of the current global structure, and the interaction energies being calculated using a cost function as defined in step (b).

the third set of residue portions provided in step (e) is selected in a random way, or while excluding any random selection method.

in step (e), the third set of residue portions comprises at least those residue portions of the first set forming the immediate environment of the one or more perturbed residue portions, the immediate environment being defined in accordance with inter-atomic distances or, optionally, with pairwise interaction energies between rotamers, calculated using a cost function as defined in step (b).

in step (f), the set of considered rotamers for each residue portion of the third set may comprise all rotamers of the set of step (c) or may be restricted to a set of rotamers for a single residue type, or may be restricted in accordance with a data set of energetic contributions, calculated using a cost function as defined in step (b).

in step (f), the rotamer selected for each residue portion of the third set has a favorable, preferably an optimal, individual contribution to the global cost of the system, in comparison with the individual contribution of the other considered rotamers for the same residue portion of the third set.

step (g) is ignored and the first acceptance criterion of step (h) is always met.

the first acceptance criterion of step (h) is met only if the global cost calculated in step (g) is more optimal than the global cost of the current global structure.

the optimization process continues until each single residue portion or each pair of residue portions each multiplet of residue portions of the first set has been included at least once into the second set of perturbed residue portions.

the number of combinations of perturbed residue portions is restricted in accordance with inter-atomic distances, or in accordance with pairwise interaction energies between rotamers, calculated using a cost function as defined in step (b).

the termination criterion of step (i) is based on a predetermined number of optimization rounds, or on a predetermined energetic threshold value, the said threshold value being compared with the difference between the most optimal global cost observed in two consecutive optimization rounds.

in step (e) of each optimization cycle, the same second set of perturbed residue portions each in the same temporarily fixed rotameric state, and a different third set of residue portions containing only one single residue portion are provided.

one or more of steps (a) to (d) are replaced by one or more steps wherein pre-computed data is provided from a storage medium, a remote location, or a preceding application, the said pre-computed data implicitly including the actions described in the replaced steps.

Experimental Section

The FASTER method has been applied to 50 protein structures selected from the Protein Data Bank of Brooks et al. (cited supra) on the basis of their resolution (less than 1.8 Å), R-factor (less than 0.20), size (100 to 450 amino acid residues in total), sequence identity (less than 25% identity with any other structure in the test set), number of protein chains (only monomeric single chain molecules were selected) and ligands (structures with no or small ligands were chosen). Prior to the FASTER experiments, these proteins had been side-chain modelled using the original DEE algorithm of Desmet et al. (cited supra). More specifically, the GMEC for all side chains of each protein as well as the accompanying total energy had been determined on beforehand and stored on disk. These data provide an assessment of the quality of the FASTER algorithm as they enable a systematic comparison of the FASTER results with the theoretically best possible results, i.e. the conformation of the global minimum. The results on the 50 test structures are hereafter described in three different ways, i.e. (i) a detailed analysis of a representative modelling experiment on a single protein structure, (ii) a statistical comparison between the FASTER and DEE results with respect to accuracy and computing time and (iii) a statistical analysis of the accuracy of the FASTER and DEE method when comparing the modelled structures with the experimentally determined structures.

Table 1 shows a complete list of the PDB codes that were downloaded from the official PDB Internet site (www.rcsb.org/pdb/). All structures have been prepared by the modeling package of Delhaise et al., *J. Mol. Graph.* (1984) 2:103-106 as follows. First, the program took the PDB-formatted co-ordinates file as input. Missing hydrogen atoms were added automatically in standard geometry. Next, the structure was subjected to 100 steps of steepest descent energy minimisation to remove possible close contacts between atoms. Finally, all hetero groups, including water molecules, were removed and the resulting atomic co-ordinates were stored on disk in binary format for rapid retrieval in later modelling experiments.

All 50 structures have been processed by the DEE algorithm in order to determine the GMEC of the rotatable side chains. For this purpose, the latest version of the DEE algorithm was used as described by De Maeyer et al. in *Fold & Des.* (1997) 2:53-66. As a result of these operations, 50 files were stored on disk containing a reference to the modelled structure (PDB code), the type of force field used in the energy calculations, the rotamer library used, user-defined optimisation parameters and, importantly, the final GMEC rotamers as found by the DEE computations as well as the accompanying total energy of the protein in the GMEC.

The energy function used in both the DEE and FASTER experiments comprises the usual terms for bond stretching, bond angle bending, a periodic function for the torsion angles, a Lennard-Jones potential for the non-bonded atom pairs, a 10-12 potential for hydrogen bonds and a coulombic function for charged atoms. The dielectric constant is of the distance dependent type, meaning that it is set equal to $r_{ij}$, the distance between two atoms i and jas defined by Warshel & Levitt in *J. Mol. Biol.* (1976) 103: 227-249. The energy parameters needed in conjunction with the above-mentioned energy function are derived from the CHARMM library of Brooks et al. (cited supra) and include values for explicit hydrogen atom contributions.

In all experiments, the list of residues to be modelled, hereafter called rotatable or flexibly treated side chains, contained all side chains present in the PDB input file except GLY, ALA, PRO and CYS. All atoms of these amino acid residues were kept fixed throughout the experiments, which was conveniently accomplished by including them into the template. Furthermore, also the $C_\beta$-atoms of all residues were considered as being inherently part of the main chain and were therefore incorporated into the template. The main-chain atoms themselves were included in the set of template atoms. The flexibly treated side chains were placed back onto the backbone structure in standard bond angle and bond length geometry during the initialisation stage of both the DEE and FASTER algorithms. This geometry remained unaltered during all experiments since only torsional changes in conformation (around single bonds) were carried out. Also the main-chain structure or, rather, the co-ordinates of the template atoms remained unchanged throughout all experiments.

The rotamer library applied corresponds to the "large library" described in De Maeyer (cited supra), i.e. a backbone-independent library containing 859 elements to represent the theoretically possible side-chain conformations of the 20 natural amino acid types: GLY has 0 rotamers, ALA 1, PRO 0, CYS 0 whereas CSH 9, SER 9, THR 9, VAL 4, LEU 17, ILE 7, ASP 9, ASN 18, HIS (two protonated and one neutral form) 175, PHE 125, TYR 100, TRP 150, MET 24, GLU 24, GLN 60, LYS 56 and ARG 62. Amino-terminal and carboxy-terminal side chains are treated separately but have an identical set of rotamers. Each rotamer is represented in the library as a set of maximally four torsion values, one for each dihedral side-chain angle present in the corresponding residue type, which together unambiguously define a specific side-chain conformation if standard bond geometry is used. As an example, a fragment of this library is provided in FIG. 7.

Figure 4:
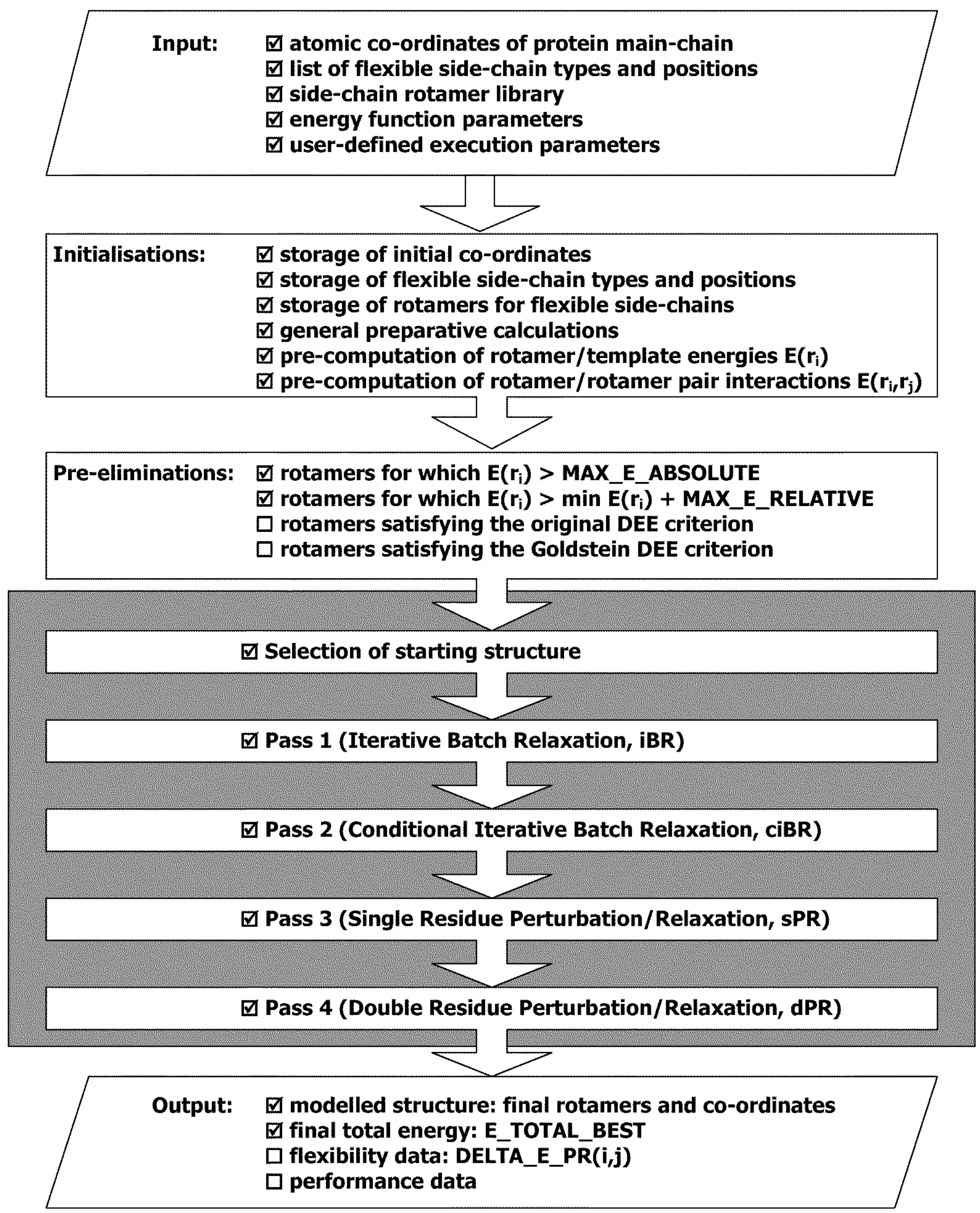
FIG. 4 shows a flow diagram of a complete FASTER method in its preferred embodiment, wherein the grey frame shows the pure FASTER routines. Steps required for optimal performance are marked ☑ whereas optional steps are marked □. In less preferred embodiments, many steps can be switched off, depending on the user's needs.

In all experiments, the same user-defined parameters have been used according to the settings for the preferred embodiment described before. Concretely, the following parameter values were assigned: MAX_E_ABSOLUTE=30 kcal $mol^{-1}$, MAX_E_RELATIVE=10 kcal $mol^{-1}$, MAX_CYCLES_P1=10, MAX_CYCLES_P2=20, ACC_PROB=0.8 in pass2 and ACC_PROB=1.0 in passes 3 and 4, N_REPEATS_P2=10, MAX_CYCLES_P4_PRE=1. The pairs restriction method in pass 4 was the method based on the distance between $C_\beta$-atoms. All four passes of the FASTER method were executed in sequential order (as illustrated in FIG. 4). The DEE pre-eliminations were switched on. No flexibility analysis was performed since the experiments described were intended to illustrate the usefulness of the perturbation/relaxation/evaluation principle and the correctness and performance of the FASTER method based on this principle.

In order to exemplify the features of the FASTER method, results of the FASTER modelling of 1AKZ (uracil-DNA glycosylase) are now described in detail. The crystallographic resolution of the PDB structure (determined by X-ray diffraction) is 1.57 Å and the refinement factor is 0.189 (as seen from Mol et al., *Cell* (1995) 80:869-878. After reading the PDB file, 2135 H-atoms were added in standard geometry. Next, 100 steps of steepest descent energy minimisation were performed which reduced the potential energy from −250 kcal $mol^{-1}$ in the X-ray structure to −2210 kcal $mol^{-1}$ in the energy minimised structure, while the RMSD was only 0.108 Å. All 185 solvent molecules were then removed and no other hetero groups were present so that the resulting structure consisted only of protein atoms. This structure was stored on disk for usage in the DEE and FASTER experiments. The two separate experiments with the DEE and FASTER method were performed using the same extended rotamer library (859 elements), the same starting structure (from disk), the same list of rotatable side chains, adapted to standard geometry (177 non-GLY, -ALA, -PRO, or -CYS residues out of the 223 residues in total) and identical parameters for pre-elimination (MAX_E_ABSOLUTE=30 kcal $mol^{-1}$, MAX_E_RELATIVE=10 kcal $mol^{-1}$).

Using the settings mentioned, there were 9123 rotamers distributed over the 177 rotatable side chains (about 50 per residue, on average) which involved $7\times10^{254}$ possible global structures. The DEE method succeeded to find the unique optimal solution, i.e. the GMEC, after 76148 CPU-sec (~21 CPU-hour) on a SGI Indigo2 R10000 single processor workstation. The final structure had a total energy of −1272.2 kcal $mol^{-1}$ and was not further energy minimised. It was stored on disk for later comparison with the FASTER modelled structure.

Figure 8:
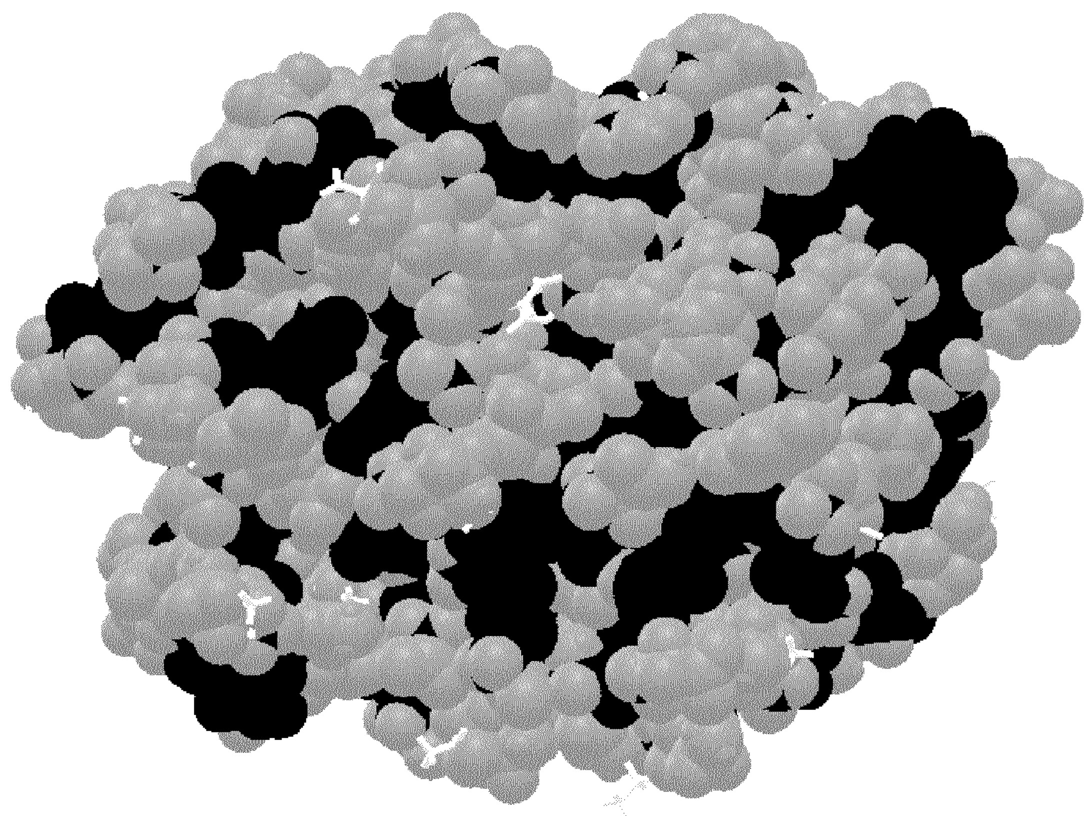
FIG. 8 shows a graphical representation of the molecular structure of 1AKZ (uracil-DNA glycosylase) as generated by the FASTER method of the present invention (see EXPERIMENTAL SECTION, REPRESENTATIVE EXPERIMENT). All atoms used in the computations are shown by spheres centred on the atomic co-ordinates. Black spheres represent template atoms (held fixed throughout the computations) while grey spheres are used to show the final, modelled positions of the side-chain atoms. For comparison, the experimentally determined structure of 1AKZ has been superimposed on the modelled structure in a sticks representation (covalent bonds between atomic centres are visualised by white sticks). Since the vast majority of the predicted atomic positions do not deviate more than the size of their atomic radius from the known positions, most of the sticks are hidden in the spheres. Consequently, only significant differences between the predicted and known structure are visible.

The FASTER experiment on 1AKZ was performed without any interference from the DEE results (all comparisons were done afterwards). The preferential settings were applied as described above. The initialisation routines (see FIG. 4) consumed 6.1 CPU-sec, excluding the energy pre-calculations. The latter took 7.1 CPU-sec and 27.4 CPU-sec for the rotamer/template interactions and the pair energies, respectively. The pre-eliminations on basis of an absolute and relative cut-off for the rotamer/template interactions of 30 and 10 kcal $mol^{-1}$, respectively, succeeded in reducing the total number of rotamers from 9123 to 3615. This number was further reduced by the DEE pre-eliminations to 2310 rotamers after 1.7 and 8.8 CPU-sec, respectively. (For comparison, in the DEE experiment only 1432 rotamers were left at this stage but this required 3416 CPU-sec). Next, the actual FASTER computations were started. The Eisenmenger starting structure was computed by storing, for each rotatable side chain, the rotamer with the lowest interaction energy with the template (ignoring pair energies) in the initial IMEC data set. This IMEC had a total energy, E_TOTAL, of $2.9\times10^{10}$ kcal $mol^{-1}$ which indicates the presence of several severe atomic clashes. Comparison with the GMEC results showed that 60.5% of all side chains assumed the GMEC rotamer. The execution of pass 1 (iBR) needed only 0.3 CPU-sec and resulted in a relatively small reduction of E_TOTAL to $1.2\times10^{8}$ kcal $mol^{-1}$. Yet 74.0% of the side chains were in the GMEC. In the 7th iteration cycle, the system started oscillating between two conformations having an energy of $1.2\times10^{8}$ kcal $mol^{-1}$ and $1.1\times10^{10}$ kcal $mol^{-1}$, respectively. Pass 2 (ciBR) was able to escape from this oscillatory state and could remove the strongest inter-atomic conflicts, which can be inferred from E_TOTAL=−1017.9 kcal $mol^{-1}$ and a GMEC score of 81.9%. This IMEC occurred in the 2nd of 10 repeats which required 4.7 CPU-sec in total. Pass 3 (sPR) was also very effective in further optimising the structure as it resulted in an IMEC with E_TOTAL=−1271.2 kcal $mol^{-1}$. For the whole protein, this is only 1 kcal $mol^{-1}$ above the energy of the GMEC (0.006 kcal $mol^{-1}$ per residue, on average). 95.5% of the side chains were already in the GMEC after pass 3. Three perturbation rounds were performed, the first yielding 22 energetical improvement events, the second 1 and the third none, which gave an exit condition. All calculations in pass 3 needed only 4.9 CPU-sec. Pass 4 was the slowest routine, consuming 93.1 CPU-sec. The identification of rotamers to be ignored in the pairwise perturbations (see ALGORITHMICAL OPTIMISATIONS, equations 4 and 5) gave 1075 remaining rotamers (1235 ignored). The perturbations on the basis of pairwise combinations of these rotamers, followed by relaxation, resulted in 3 energetic improvement events. The last one resulted in the absolute GMEC (score=100%). Comparison of the rotamers clearly showed that the FASTER method had identified the true GMEC. The total computing time for the entire modelling was 156.1 CPU-sec, which means that the FASTER method was 488 times faster than the DEE method. The final modelled structure was stored on disk in PDB-format and the coordinates of this structure were used to construct the graphical representation shown in FIG. 8. When superimposing the experimentally determined with the modelled structure, it is possible to obtain a qualitative appreciation of their resemblance. FIG. 8 shows that the side chains in the modelled structure match very well with those in the known structure, although all knowledge about the latter was completely ignored during the computations. We next describe a more statistical, quantitative analysis of FASTER-modelled structures in comparison with DEE-modelled structures and experimentally determined structures.

Statistical Comparison of Faster and Dee Structures

Figure 9:
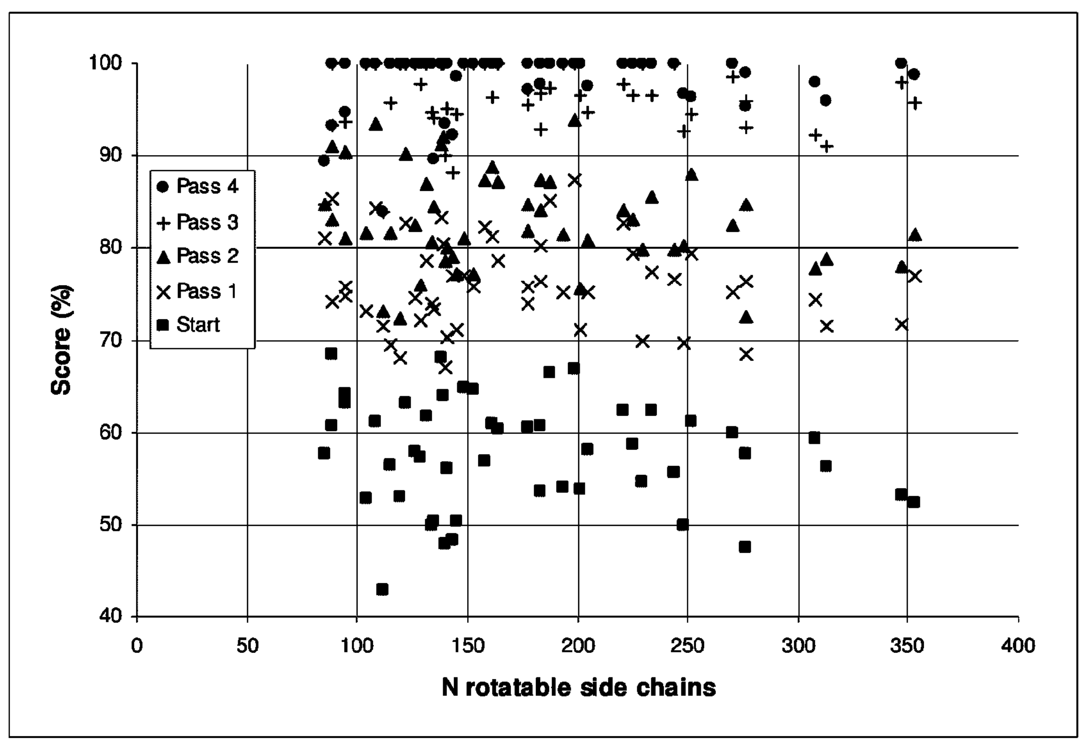
FIG. 9 shows the side-chain conformation prediction scores for 50 protein structures after each pass of the FASTER method of this invention. Prediction scores are here expressed as the percentage of side chains that are exactly in the GMEC as computed by the DEE algorithm. The size of the proteins is expressed as the number of flexibly treated residues (N rotatable side chains, i.e. all residues except GLY, ALA, PRO, CYS). Numeric average values and standard deviations are given in table 2.

FIG. 9 shows for each protein the percentage of side chains that are exactly in the GMEC after each consecutive pass of the FASTER algorithm. Table 2 shows the average values and standard deviations for the Eisenmenger starting structure and after each pass. In this figure, scores are plotted as a function of the size of the proteins expressed in terms of the number of rotatable side groups. For each pass including the starting conformation it was found that the scores are independent of the protein size. It is also clearly seen that each individual pass leads to a gradual and significant improvement of the global conformation. For the starting structure, where each residue was assigned the rotamer with the best possible interaction with the template, ignoring other side chains, the average score amounted 57.8% with a standard deviation of 5.8%. Application of pass 1 (iBR) led to the most significant improvement by nearly 20% to an average score of 76.2±5.0%. Pass 2 (ciBR) further increased the score to 83.0±5.3%. The third pass (sPR) turned out to be the most effective, considering the fact that the majority of the side chains were already in the GMEC. The average score increased by 13.1% to 96.1±3.9% and in 17 out of the 50 cases the entire structure was identical to the global minimum. Finally, pass 4 yielded a score of 98.2±3.4% on average and the GMEC was reached for 32 proteins.

Another way to evaluate the FASTER results is by measuring the volume overlap of each side chain with the GMEC. For this purpose, the volume overlap criterion was used as described in detail in De Maeyer (cited supra). Briefly, two side-chain conformations were assumed to be equivalent when they showed a volume overlap larger than 70%. When using this criterion it was again observed that the average prediction scores gradually increased as a function of the different passes (see table 2). However, all scores based on the volume overlap criterion were significantly higher than those based on the identity with the GMEC. This obviously arises from the fact that the overlap criterion is less restrictive (but probably more significant) than the identity criterion. The average volume-based scores varied from 75.2% for the starting structures, to 85.1% in pass 1, 90.0% in pass 2, 97.7% in pass 3, to 98.9% for the final structures after pass 4.

Figure 10:
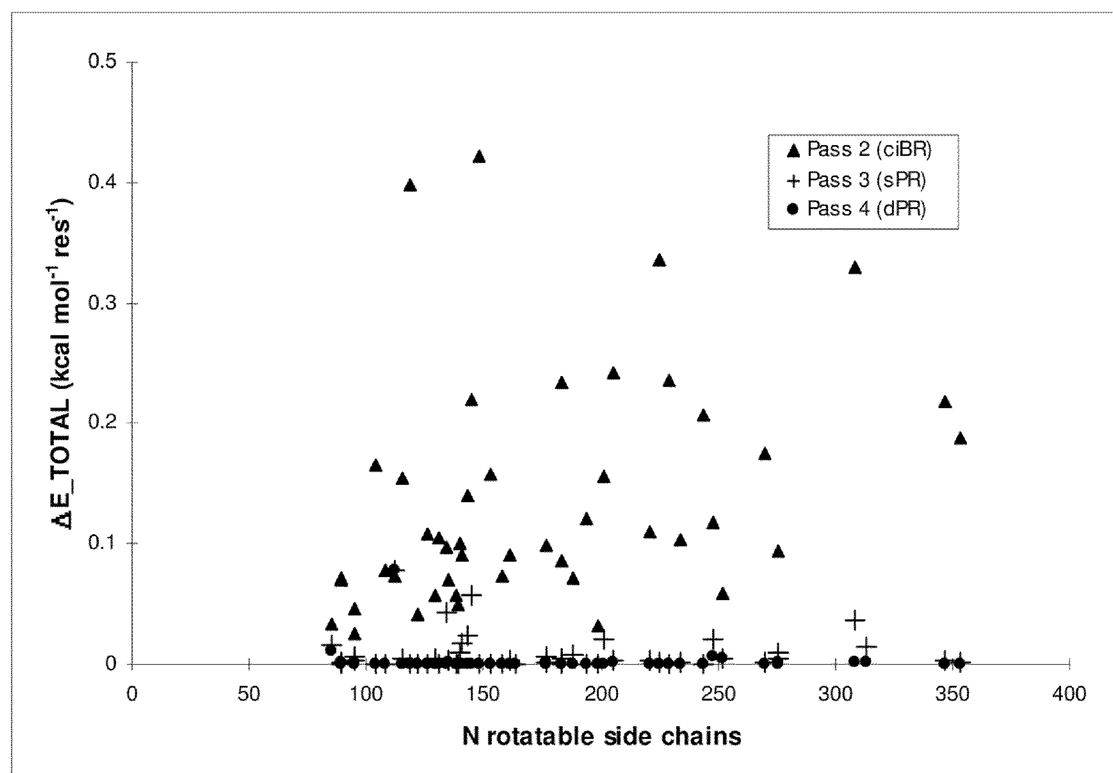
FIG. 10 shows, for the 50 test proteins of FIG. 9, the difference in total energy between the FASTER-computed structures as obtained after passes 2-4 and the DEE-computed GMEC. The energy differences (ΔE_TOTAL) are expressed in kcal $mol^{-1}$ per rotatable residue and plotted as a function of the protein size, more specifically the number of rotatable side chains in the protein.

An even more significant measure of the quality of the computed structures is the evolution of the total energy (E_TOTAL) after each pass. FIG. 10 and table 2 show the difference in total energy between the structures obtained after passes 2-4 and the GMEC. All values have been divided by the number of rotatable side chains in the protein since large proteins obviously contain more deviations which makes the difference in E_TOTAL size-dependent. The starting structures and the conformations obtained after pass 1 always contained severe atomic overlaps, yielding strongly positive energy values with a large spread. In the majority of the cases the worst clashes had been removed in pass 2 but the average difference with the GMEC stayed rather high at 0.13±0.09 kcal $mol^{-1}$ $res^{-1}$. Pass 3 and 4 drastically reduced the energy differences to 0.008±0.015 and 0.002±0.011 kcal $mol^{-1}$ $res^{-1}$, respectively. These values mean that for a medium-sized protein of 200 rotatable residues the energy of the global minimum can usually be approximated to about 1.5 kcal $mol^{-1}$ after the single perturbation/relaxation routine (pass 3) and 0.5 kcal $mol^{-1}$ by the full FASTER method. Since the total energy of such protein E_TOTAL is usually in the order of $-10^3$ kcal $mol^{-1}$, these values can be considered as extremely small if not negligible. This also justifies the assertion that, in a less preferred but more practical embodiment, the relatively slow double perturbation/relaxation routine (pass 4) can be skipped without sacrificing much in quality.

Figure 11:
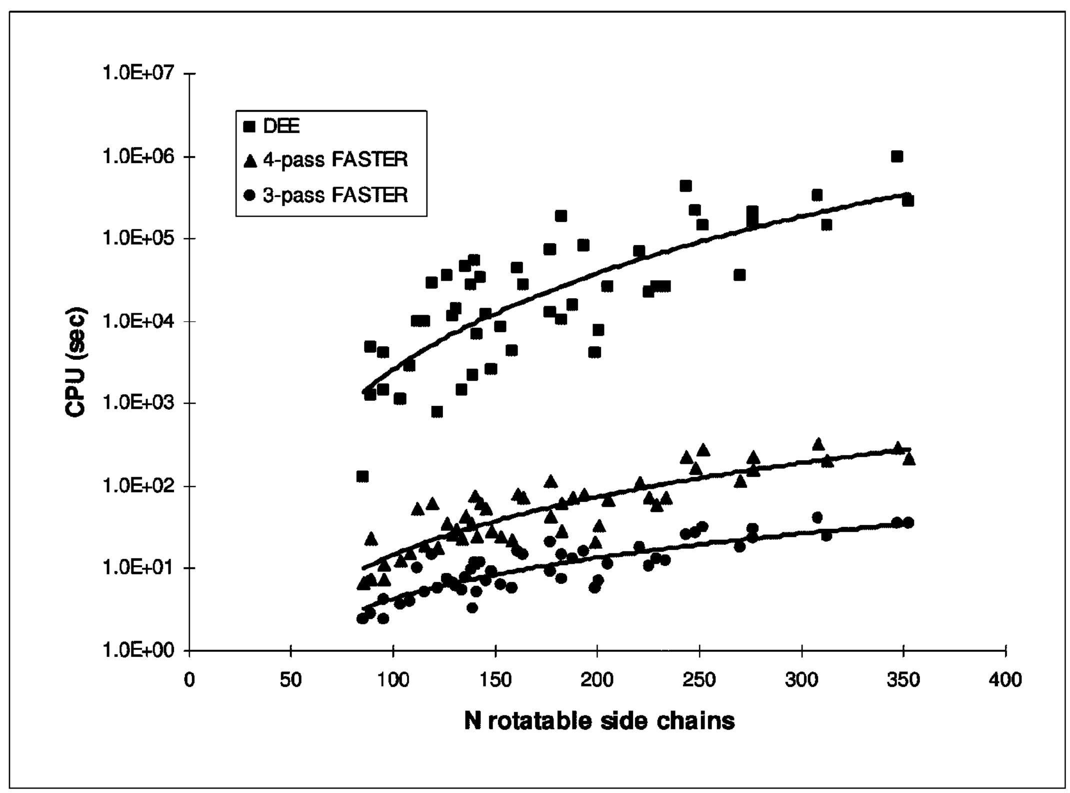
FIG. 11 shows, for the 50 test proteins of FIG. 9, the central processing unit (CPU) times required to model the side chains using the DEE method (squares) and the 4-pass (triangles) and 3-pass (circles) FASTER method on comparable computers. In order to show the net computational requirements of the modelling routines, the CPU times for the initialisation and pre-elimination of rotamers is subtracted from the total values. All values are expressed in seconds and plotted, on a logarithmic scale, as a function of the number of rotatable side chains in the protein.

FIG. 11 shows the computational time required for the modelling of each protein using the DEE algorithm and the 3- and 4-pass FASTER algorithm. Because of the extreme differences in CPU-times, the values were plotted on a logarithmic scale. Analysis of the data showed that the CPU-times scale with the number of rotatable residues to the power of 3.64, 2.39 and 1.74 for the DEE method and the 4- and 3-pass FASTER method, respectively. While the CPU-times for the DEE method lie in the range of 20 CPU-min for the smallest proteins up to 2 CPU-days for the very largest, the 4-pass FASTER method consumes less than 10 CPU-sec for the smallest and 3 CPU-min for the largest proteins. This means that the full FASTER method is roughly 100 to 1000 times faster than the DEE method, depending on the protein size. When using the 3-pass FASTER method, the computational times were reduced by another factor of 3 to 8. Then for even the largest proteins, the structure could be obtained in less than 0.5 CPU-min.

Comparison with Experimental Structures

Table 3 herein-above lists results obtained for three methods and for the template-based method, which is similar to the Eisenmenger method. The predicted structures are evaluated using three applicable criteria and separate values are given for the buried and for all side chains.

On basis of the 70% volume overlap criterion, the DEE algorithm is found to place 71.3±6.0% of all rotatable side chains in a correct conformation. For the buried side chains an average score of 85.2±5.1% was obtained. The side-chain RMSD with the X-ray structure was 1.55±0.22 Å for all and 1.02±0.19 Å for the buried residues. Another evaluation method is the $\chi_{1,2}$-criterion which considers a side-chain conformation as correct if both the $\chi_1$ and $\chi_2$ angles are within 40° from the values observed in the experimental structure. In this study it was found that the $\chi_{1,2}$ and the overlap criterion yielded very similar results when the scores were averaged over a large test set. However, the two criteria often showed large differences for individual proteins, up to 8.9% for buried residues and up to 4.2% for all residues. Both evaluation criteria are therefore suitable to judge the prediction quality of a given method when tested on a large set of proteins, but for individual structures (or a small test set) the more significant overlap criterion is to be preferred.

Comparison of the prediction accuracy of the 3-pass and 4-pass FASTER and the DEE method is extremely important. Table 3 clearly shows that all three methods yield nearly identical scores when the modelled structures are compared with the experimental structures. Even the 3-pass FASTER method gives a prediction score which is equivalent with the DEE score, irrespective of the evaluation criterion or the degree of burial. This might seem somewhat surprising as it was shown above that on average 3.9% of the side chains modelled by the 3-pass FASTER method were not in the GMEC and that 2.3% of them did not significantly overlap with the GMEC (see table 2). These differences completely disappear when the resulting structures are evaluated against the X-ray determined structures. It can therefore be concluded that the accuracy of the predictions is essentially identical when using the DEE method or the 3- or 4-pass FASTER method. Furthermore, since the 3-pass and 4-pass FASTER methods are perform several orders of magnitude faster, they will be preferred over the DEE method unless the absolute GMEC is required.

Flexibility Analysis

The molecular structure referred to as 1ZIA (PDB-code of pseudoazurin) has been selected to illustrate the potential of the FASTER method to assess the conformational flexibility of individual side chains. Here, conformational flexibility is to be understood as the energetically allowed conformational variation given the (fixed) molecular template and the considered rotamer library and energy function (see EXPERIMENTAL CONDITIONS). Formally, the flexibility coefficient of a side chain i,f(i), can be defined as $$f(i)=(N_{allowed}(i)-1)/(N_{library}(i)-1) \quad \text{(eq. 7)}$$

where $N_{library}(i)$ is the total number of rotamers known in the rotamer library for residue i and $N_{allowed}(i)$ is the number of rotamers r for residue i for which $$\text{DELTA\_}E\text{\_}PR(i,r)<\text{MAX\_DELTA\_}E\text{\_}PR \quad \text{(eq. 8)}$$

The values DELTA_E_PR(i,r) are calculated in the sPR pass in accordance with equation 6 (see USE OF sPR DATA TO PREDICT CONFORMATIONAL FLEXIBILITY), whereas MAXDELTA_E_PR is a user-defined parameter. In the currently described experiment on 1AKZ, the parameter MAX_DELTA_E_PR was set equal to 5 kcal $mol^{-1}$, which means that all rotamers having a perturbation energy less than 5 kcal $mol^{-1}$ were considered as energetically compatible with the structure. Equation 7 defines a linear relationship between the flexibility coefficient, ranging between 0 and 1, and the number of allowed rotamers, ranging between 1 and the total number of rotamers known in the rotamer library for a given residue. For example, suppose that at a given residue position i, a VAL residue were located, which can be represented by 3 library rotamers in total, and that this VAL could adopt 2 energetically favourable rotamers at the given position, this would correspond to a flexibility coefficient f(i)=(2−1)/(3−1)=0.5 or 50%.

For the sake of comprehensiveness, all rotatable side chains in a structure can be easily classified as either rigid, moderately flexible or flexible. The class of rigid side chains is preferably constructed by considering those side chains having a flexibility coefficient less than 5% ($f<0.05$). Flexible side chains are preferably those having more than one third of energetically compatible rotamers ($f>0.34$). The remainder of the side chains are preferably included in the set of moderately flexible side chains ($0.05<f<0.34$). Both the assignment of side chains to flexibility classes and the setting of the bounds for each of these classes result from pragmatical considerations and should not be considered as essential features of the method.

Figure 12:
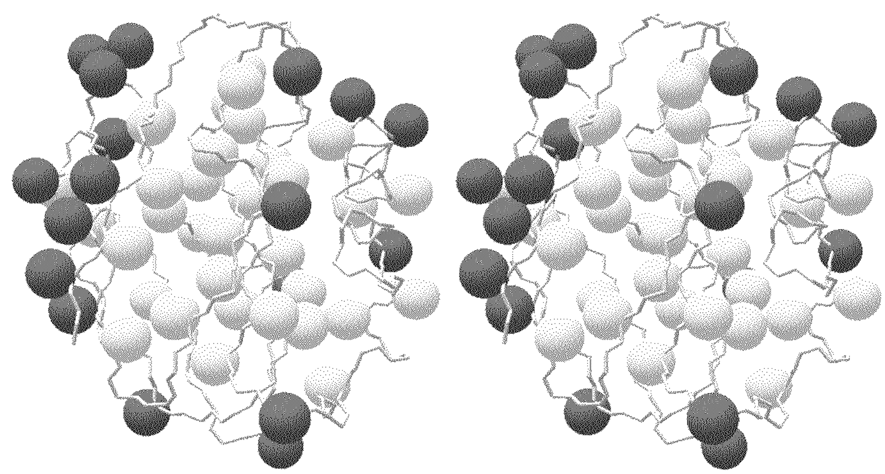
FIG. 12 shows the results of a flexibility analysis of the protein referred to by the PDB code 1ZIA. The residues classified by the FASTER method as being rigid (flexibility coefficient $f<0.05$) or flexible ($f>0.34$) are depicted by light or dark spheres respectively. All spheres are mapped onto the $C_\beta$-atom of the side chains concerned. Moderately flexible residues are not shown. The protein main chain (N-, $C_\alpha$- and C-atoms) is represented by a sticks model (thin wire). The atoms themselves are not shown. Flexibility coefficients have been calculated according to equations 7 and 8. This figure shows that rigid side chains are located mainly in the core of the protein, whereas the side chains predicted to be flexible are almost exclusively solvent-oriented.

When using aforementioned settings, analysis of the flexibility data on 1AKZ resulted in the following conclusions: out of a total of 85 rotatable side chains, 34 could be classified as flexible, whereas 17 rotatable side chains were inherently rigid. A striking observation was that nearly all of the side chains that were classified as flexible had a typical polar character (e.g. the acidic, basic, or OH-containing residue types) whereas the more rigid side chains were usually apolar (e.g. aliphatic or aromatic). When the residues belonging to each of the latter two classes were identified in the 3D-structure, it was found that the typically flexible side chains were located exclusively among the solvent-oriented side chains, while the rigid side chains were mainly clustered in the core of the protein (see FIG. 12). The moderately flexible side chains were essentially distributed over the whole molecule, although with some preference to appear at the boundary of the protein. These findings are consistent with the general idea that the atomic packing at the interior of a protein is very dense and specific, whereas the packing at the exterior layer is much less dense, resulting in fewer atomic constraints and, consequently, a greater conformational freedom. The present invention can therefore provide a valuable tool to explore and/or quantify this important property.

The invention claimed is:

1. A method for generating a model of the molecular structure of a biomolecule and information related to the said molecular structure, the method being executable by a computer under the control of a program stored in the computer, and comprising the steps of:

(a) receiving a representation of a molecular structure of said biomolecule comprising a plurality of residue portions, and forming from the plurality of residue portions a first set of residue portions, the remainder of the molecular structure being designated as a template;

(b) defining an energetic cost function which assigns a quantitative energetic cost to any global structure of the said biomolecule and to any set of residue portions thereof;

(c) providing a set of rotamers for each residue portion of the first set of residue portions formed in step (a) wherein each rotamer is fixed in a rotameric state;

(d) assigning one rotamer from the set of rotamers of step (c) to each residue portion of the first set formed in step (a), thereby defining a first current global structure for said biomolecule;

wherein the method further comprises modifying said first current global structure by repeating an optimization cycle, wherein each optimization cycle comprises the following steps (e) through (i):

(e) providing, from the first set of residue portions with assigned rotamer states of step (d), a second set of residue portions wherein the second set of residue portions have been perturbed and then temporarily fixed in a rotameric state selected from those provided in step (c); and providing, from the first set of residue portions with assigned rotamer states of step (d), a third set of residue portions that have not been perturbed;

(f) relaxing each residue portion of the third set towards an energetically more optimal state by:

(f1) considering at least some rotamers of the set of step (c);

(f2) calculating, for each considered rotamer, while using the energetic cost function of step (b), its individual contribution to the energetic cost of the global structure consisting of the template, the one or more residue portions of the second set in their temporarily fixed rotameric states, the residue portions of the third set, and the remaining residue portions of the first set, if any, in their assigned rotameric states, and (f3) selecting, from the rotamers considered in step (f1), the rotamer with the most optimal individual contributions calculated in step (f2);

(g) calculating, using the energetic cost function of step (b), the cost of the global structure consisting of the template, the one or more residue portions of the second set in their temporarily fixed rotameric states, the one or more residue portions of the third set in their rotameric states selected in step (f3), and the remaining residue portions of the first set, if any, in their assigned rotameric states;

(h) defining a second current global structure by (h1) establishing a first acceptance criterion by comparing the global cost calculated in step (g) with the global cost, calculated using the energetic cost function of step (b), of the first current global structure of step (d), and (h2) if said first acceptance criterion is met, assigning by way of replacement, for each residue portion of the second set, the currently assigned rotamer with the rotamer temporarily fixed in step (e) and, for each residue portion of the third set, the currently assigned rotamer with the rotamer selected in step (f3);

and (i) determining whether a predetermined termination criterion has been reached, wherein, if said predetermined termination criterion has been reached, said optimization cycle is terminated;

and wherein the method further comprises:

(j) outputting to a display or to a user in a user-readable format, a representation of a second current global structure defined in step (h) or the global cost calculated in step (g).

2. A method according to claim 1, wherein the representation outputted in step (j) is a global or partial representation of a three-dimensional structure of said biomolecule.

3. A method according to claim 1, wherein the number of residue portions in the first set present in step (a) is at least 5.

4. A method according to claim 1, wherein a combinatorial conformational space, calculated as the product of the number of rotamers provided in step (c) for each residue portion of the first set, is at least 1,000,000,000, or wherein a larger combinatorial conformational space is subdivided into smaller fractions and distributed over separate executions of the method.

5. A method according to claim 1, wherein at least 30% of the rotamers provided in step (c) for each residue portion of the first set are selected at least once for temporary fixation in step (e).

6. A method according to claim 1, wherein at least 100 perturbation steps in accordance with step (e) are performed, or wherein any larger number of perturbation steps is distributed over separate executions of the method wherein less than 100 perturbation steps are performed.

7. A method according to claim 1, wherein in step (e) the third set of residue portions comprises at least a threshold of 30% of the residue portions of the first set, and forms the immediate environment of the one or more residue portions of the second set, wherein the residue portions forming the immediate environment of the residue portions of the second set are those residue portions having at least one atom closer than 0.4 nanometer to any atom of a residue portion of the second set in the first current global structure defined in step (d) or the second current global structure defined in step (h), or wherein the same second set of residue portions, in combination with different third sets of residue portions, are distributed over different optimization cycles so as to stay below said threshold of 30%.

8. A method according to claim 1, wherein the number of said rotamers considered in the relaxation step (f1), averaged over all the residue portions of the third set provided in step (e), amounts to at least a threshold of 20% of the average number of rotamers provided in step (c) or wherein the number of rotamers provided in step (c) is made redundant so as to stay below said threshold of 20%.

9. A method according to claim 1, wherein the residue portions of the first set formed in step (a) comprise at least those atoms which undergo spatial displacement when applying the different rotamers provided in step (c), the remainder of the atoms of said biomolecule being included in the template.

10. A method according to claim 1, wherein the energetic cost function of step (b) is a function which allows calculation of a quantitative measure of the free or potential energy of a global structure of said biomolecule and a set of residue portions thereof.

11. A method according to claim 1, wherein the rotamers provided in step (c) are descriptions of potential three-dimensional structures of the residue portions of the first set, wherein for each residue portion of the first set the three-dimensional structures represent different conformations of one or more single residue types.

12. A method according to claim 1, wherein the rotamers provided in step (c) result from a computational generation of different three-dimensional structures of single residue types within the context of a molecular reference structure.

13. A method according to claim 12, wherein the rotamers provided in step (c) further result from the energetic analysis, using a cost function as defined in step (b), of the computationally generated three-dimensional structures.

14. A method according to claim 1, wherein the rotamers provided in step (c) are side-chain rotamers.

15. A method according to claim 1, wherein the rotamers provided in step (c) are combined main-chain/side-chain rotamers.

16. A method according to claim 1, wherein some rotamers provided in step (c) are eliminated on the basis of their energetic interaction, calculated using a cost function as defined in step (b), with the template defined in step (a).

17. A method according to claim 1, wherein some rotamers provided in step (c) are eliminated by applying a dead-end elimination method.

18. A method according to claim 1, wherein the assignment of rotamers in step (d) is performed while using the rotamers provided in step (c) in combination with a random selection method.

19. A method according to claim 1, wherein the assignment of rotamers in step (d) is performed while using the rotamers provided in step (c) in combination with an energetic analysis, using a cost function as defined in step (b), of the rotamers provided within the context of the template as defined in step (a).

20. A method according to claim 1, comprising an additional step in which the energetic interactions are calculated between the rotamers provided in step (c) and the template defined in step (a) and/or between pairs of rotamers of different residue portions of the first set, wherein the energetic cost function of step (b) is used for said calculation, and wherein the calculated energetic interactions are used in an optimization cycle.

21. A method according to claim 1, wherein the second set of residue portions provided in step (e) is randomly selected from the first set of residue portions.

22. A method according to claim 1 wherein the biomolecule comprises a residue sequence, and wherein, in step (e), the second set of residue portions is selected from the first set of residue portions in accordance with the residue sequence of the biomolecule.

23. A method according to claim 1 wherein, in step (e) of each optimization cycle, the second set of residue portions consists of a single residue portion or two residue portions.

24. A method according to claim 1 wherein, in step (e) of each optimization cycle, the second set of residue portions consists of three or more residue portions.

25. A method according to claim 1 wherein, in step (e), the temporarily fixed rotameric state of each residue portion of the second set is randomly selected from the set of step (c).

26. A method according to claim 1 wherein, in step (e), the temporarily fixed rotameric state of each residue portion of the second set is selected from the set of step (c) while excluding any random selection method.

27. A method according to claim 1 wherein, in step (e), the temporarily fixed rotameric state of each residue portion of the second set is selected from the set of step (c) while excluding any rotamer R for a perturbed residue portion P, for which a first energetic term A is higher than a second energetic term B, the term A being calculated as the interaction energy of the rotamer R with the template augmented with the sum of the best possible pairwise interaction energies with R, given the rotamers provided in step (c), and the term B being calculated as the interaction energy of any rotamer S for the residue portion P with the template, augmented with the pairwise interaction energies with the rotamers of the current global structure, and the interaction energies being calculated using a cost function as defined in step (b).

28. A method according to claim 1, wherein the third set of residue portions provided in step (e) is randomly selected.

29. A method according to claim 1, wherein the third set of residue portions provided in step (e) is selected while excluding any random selection method.

30. A method according to claim 1 wherein, in step (e), the third set of residue portions comprises at least those residue portions of the first set forming the immediate environment of the one or more residue portions of the second set.

31. A method according to claim 30, wherein the immediate environment is defined in accordance with pairwise interaction energies between rotamers, calculated using a cost function as defined in step (b).

32. A method according to claim 1 wherein, in step (f1), the set of considered rotamers for each residue portion of the third set comprises all rotamers of the set of step (c).

33. A method according to claim 1 wherein, in step (f1), the set of considered rotamers for each residue portion of the third set is restricted to a set of rotamers for a single residue type.

34. A method according to claim 1 wherein, in step (f1), the set of considered rotamers for each residue portion of the third set is restricted in accordance with a data set of energetic contributions, calculated using a cost function as defined in step (b).

35. A method according to claim 1, wherein the first acceptance criterion of step (h1) is met only if the global cost calculated in step (g) is more optimal than the global cost of the first current global structure.

36. A method according to claim 1, wherein the optimization cycle is repeated until each single residue portion of the first set has been included at least once into the second set of residue portions.

37. A method according to claim 1, wherein the optimization cycle is repeated until each pair of residue portions of the first set has been included at least once into the second set of residue portions.

38. A method according to claim 37, wherein the number of combinations of residue portions of the second set is restricted in accordance with inter-atomic distances.

39. A method according to claim 37, wherein the number of combinations of residue portions of the second set is restricted in accordance with pairwise interaction energies between rotamers, calculated using a cost function as defined in step (b).

40. A method according to claim 36, wherein the termination criterion of step (i) is based on a predetermined number of optimization cycles.

41. A method according to claim 36, wherein the termination criterion of step (i) is based on a predetermined energetic threshold value and wherein said threshold value is compared with the difference between the most optimal global cost observed in two consecutive optimization cycles.

42. A method according to claim 1 wherein, in step (e) of each optimization cycle, the same second set of residue portions each in the same temporarily fixed rotameric state, and a different third set of residue portions containing only one single residue portion are provided.

* * * * *